(12) United States Patent
Okubo et al.

(10) Patent No.: US 7,442,729 B2
(45) Date of Patent: Oct. 28, 2008

(54) COMPOSITION OF EPOXY RESIN, POLYPHENOLIC COMPOUND AND TRISUBSTITUTED PHOSPHONIONPHENOLATE SALT

(75) Inventors: Akiko Okubo, Kanagawa (JP); Yoshiyuki Goh, Kanagawa (JP); Yoshihito Akiyama, Kanagawa (JP); Hiroshi Hirose, Kanagawa (JP); Hirotaka Nonaka, Kanagawa (JP); Maki Sugawara, Kanagawa (JP)

(73) Assignee: Sumitomo Baeklite Company Limited, Tokyo (JP)

( * ) Notice: Subject to any disclaimer, the term of this patent is extended or adjusted under 35 U.S.C. 154(b) by 361 days.

(21) Appl. No.: 11/410,266

(22) Filed: Apr. 25, 2006

(65) Prior Publication Data

US 2006/0258822 A1    Nov. 16, 2006

Related U.S. Application Data

(62) Division of application No. 10/453,868, filed on Jun. 4, 2003, now Pat. No. 7,074,738.

(30) Foreign Application Priority Data

Jun. 5, 2002 (JP) ............................. 2002-164842
Sep. 30, 2002 (JP) ............................. 2002-287225

(51) Int. Cl.
*C08K 3/36* (2006.01)
*C08L 63/02* (2006.01)
*C08L 63/04* (2006.01)

(52) U.S. Cl. ................. 523/466; 257/793; 525/481; 525/523

(58) Field of Classification Search .................. None
See application file for complete search history.

(56) References Cited

U.S. PATENT DOCUMENTS

| | | | |
|---|---|---|---|
| 3,674,854 A | 7/1972 | Starnes, Jr. | |
| 4,171,420 A | 10/1979 | Doorakian et al. | |
| 4,302,574 A | 11/1981 | Doorakian et al. | |
| 4,395,574 A | 7/1983 | Doorakian et al. | |
| 4,477,645 A | 10/1984 | Doorakian et al. | |
| 4,540,823 A | 9/1985 | Doorakian et al. | |
| 4,939,112 A | 7/1990 | Bennett | |
| 6,306,792 B1 | 10/2001 | Miyake et al. | |
| 6,664,344 B1 * | 12/2003 | Oki et al. | 525/481 |
| 2001/0037003 A1 | 11/2001 | Miyake et al. | |

FOREIGN PATENT DOCUMENTS

| | | |
|---|---|---|
| EP | 0 019 852 | 12/1980 |
| EP | 0 362 854 | 4/1990 |
| EP | 1 130 041 | 9/2001 |
| JP | 10-025335 | 1/1998 |
| JP | 2001-098053 | 4/2001 |
| JP | 2001-98053 A * | 4/2001 |

OTHER PUBLICATIONS

Bestmann, H.J., et al., "Eine neue Variante der Smiles-Umlagerung", Liebigs Ann Chem., vol. 716, 1968, pp. 98-101, XP009016787.

* cited by examiner

*Primary Examiner*—Robert Sellers
(74) *Attorney, Agent, or Firm*—Smith, Gambrell & Russell, LLP

(57) ABSTRACT

A curing accelerator which is suitable for various curable resin compositions, an epoxy resin composition having excellent curability, storage stability and fluidity, and a semiconductor device having excellent solder cracking resistance and moisture resistance reliability are provided. The epoxy resin composition includes a compound (A) having two or more epoxy groups in one molecule, a compound (B) having two or more phenolic hydroxyl groups in one molecule, trisubstituted phosphoniophenolate or a salt thereof as a curing accelerator (C), and an inorganic filler (D).

18 Claims, No Drawings

COMPOSITION OF EPOXY RESIN, POLYPHENOLIC COMPOUND AND TRISUBSTITUTED PHOSPHONIONPHENOLATE SALT

CROSS REFERENCE TO RELATED APPLICATION

This application is a division of Ser. No. 10/453,868, filed Jun. 4, 2003, U.S. Pat. No. 7,074,738, and which is being incorporated in its entirety herein by reference.

BACKGROUND OF THE INVENTION

1. Field of the Invention

This invention relates to a curing accelerator, an epoxy resin composition and a semiconductor device, and more particularly to a curing accelerator which is suitable for thermosetting resin compositions, an epoxy resin composition containing the curing accelerator, which has excellent curability, storage stability and fluidity and is suitable for resin materials for electric and electronic parts or devices, and a semiconductor device having excellent solder cracking resistance and moisture resistance reliability.

2. Prior Art

As for a method for encapsulating semiconductor elements such as IC, LSI or the like to manufacture semiconductor devices, transfer molding using epoxy resin compositions is widely used on the ground that such a molding method is suited to low-cost mass production. Further, in order to improve properties and reliability of the semiconductor devices, epoxy resins and phenolic resins which serve as a curing agent are also required to be improved.

Meanwhile, in recent years, in the field of electronic equipment, a trend that requires compact design, light weight and high performance is still continued. In accordance with such a trend, degree of integration of semiconductor elements is increased year-by-year, and surface mounting technique for semiconductor devices is also improved. In such a trend, requirements for the epoxy resin compositions used for encapsulating semiconductor elements are becoming increasingly rigorous. Therefore, a problem arises in that the conventional epoxy resin compositions can not satisfy such rigorous requirements.

Specifically, materials used for encapsulating semiconductor elements are currently required to have improved rapid curability for realizing productivity gains as well as improved storage stability for making handling easy in transport and storage.

In general, to the epoxy resin composition for use as a resin material for electric or electronic parts or devices, an adduct of tertiary phosphine with quinones (see, e.g. JP-A-10-25335) is added as a curing accelerator for the purpose of promoting the curing reaction of resins.

However, in such a curing accelerator, a temperature region that exhibits an effect of promoting the curing reaction extends to a relatively low temperature. Therefore, even when an uncured epoxy resin and other components are simply mixed to prepare an epoxy resin composition, the curing reaction of the epoxy resin composition partially proceeds due to heat generated in the system or heat added from an external source. Also, even after mixing is completed, the curing reaction further proceeds while the epoxy resin composition is being stored at room temperature.

Such partial proceedings of curing leads to increased viscosity or lowered fluidity of the epoxy resin composition in a case where the epoxy resin composition is in a liquid form, and in a case where the epoxy resin composition is in a solid form, it leads to the development of viscosity therein. However, since such changes in the condition of the epoxy resin composition do not evenly occur in a strict sense, variations occur in curability of the epoxy resin composition from part to part.

Further, when such a partially cured epoxy resin composition is molded by curing it at high temperature (the word "mold" also includes the meaning of the word "form", and hereinafter "mold" is used in such a sense), troubles occur in the molding process due to its lowered fluidity, and as a result, a molded product has lowered mechanical, electrical or chemical properties.

Therefore, in a case where a curing accelerator having the possibility of lowering the storage stability of the epoxy resin composition is used, strict control of molding conditions as well as strict quality control in mixing components, and storage and transport at low temperature must be carried out. That is, handling of the epoxy resin composition containing such a curing accelerator is very delicate.

Further, another problem arises in that the solder cracking resistance of a semiconductor device encapsulated with such an epoxy resin composition is not sufficient to withstand surface mount soldering so that the moisture resistance reliability thereof is lowered. The reason is as follows. Specifically, since the semiconductor device is suddenly exposed to high temperature of 200° C. or more when it is immersed in solder or subjected to the reflow soldering process, if adhesion at an interface between a cured product of the epoxy resin composition and base components such as semiconductor elements, a lead frame and the like which are provided inside the semiconductor device is not sufficient, delamination occurs at the interface. The delamination will give rise to cracking in the semiconductor device and lower the moisture resistance reliability of the semiconductor device. Further, if the epoxy resin composition contains volatile components, cracking becomes liable to occur in the semiconductor device due to stress to be generated when the volatile components are explosively vaporized.

However, at the present, semiconductor devices manufactured by encapsulating semiconductor elements or the like with a cured product of the epoxy resin composition containing the curing accelerator described above (an adduct of tertiary phosphine with quinones) do not have sufficient solder cracking resistance and moisture resistance reliability.

Further, to improve the storage stability of the epoxy resin composition, researches on curing accelerators (so-called latent curing accelerators) which suppress changes with age in the viscosity and fluidity of the epoxy resin composition at low temperature and promote curing reaction only when heat is applied during forming or molding have been actively made. Through the researches, it is found that such a latent curing accelerator can be obtained by, for example, protecting active sites of a curing accelerator with ion pairs. As a result, various latent curing accelerators having a structure of a salt of organic acid with phosphonium ion are known (see, e.g. JP-A-2001-98053 (page 5)).

However, semiconductor devices manufactured using such a phosphonium salt as a curing accelerator also do not have sufficient solder cracking resistance and moisture resistance reliability that can withstand surface mount soldering.

Also, as another type of the latent curing accelerator, various latent curing accelerators having a structure of phosphonium-betaine salt have been proposed (see, e.g. U.S. Pat. No. 4,171,420 (pages 2 to 4)), which are intended to enable semiconductor devices to have sufficient solder cracking resistance and moisture resistance reliability that can withstand surface mount soldering. However, a problem also exists with such a latent curing accelerator in that it can not sufficiently cure a semiconductor encapsulating material currently used which contains low molecular weight epoxy resins and phenol aralkyl resins which serve as a curing agent.

SUMMARY OF THE INVENTION

Therefore, it is an object of the present invention to provide a curing accelerator which is suitable for various curable resin compositions, an epoxy resin composition having excellent curability, storage stability and fluidity, and a semiconductor device having excellent solder cracking resistance and moisture resistance reliability.

In order to achieve the object stated above, the present invention is directed to a curing accelerator to be mixed into a curable resin composition for promoting the curing reaction of the curable resin composition, wherein the curing accelerator comprises trisubstituted phosphoniophenolate or a salt thereof.

In the present invention, it is preferred that the trisubstituted phosphoniophenolate is one represented by the following general formula (1):

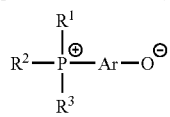
(1)

wherein $R^1$, $R^2$ and $R^3$ may be the same as or different from one another, and each contains at least one aromatic ring, and represents a substituted or unsubstituted monovalent organic group or a substituted or unsubstituted monovalent alkyl group; and Ar represents an unsubstituted divalent aromatic group or a divalent aromatic group in which at least one hydrogen atom is substituted with a substituent other than a hydroxyl group.

Further, it is also preferred that the trisubstituted phosphoniophenolate is one represented by the following general formula (2):

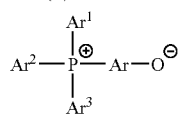
(2)

wherein $Ar^1$, $Ar^2$ and $Ar^3$ may be the same as or different from one another, and each represents a substituted or unsubstituted monovalent aromatic group; and Ar represents an unsubstituted divalent aromatic group or a divalent aromatic group in which at least one hydrogen atom is substituted with a substituent other than a hydroxyl group.

Moreover, it is also preferred that the trisubstituted phosphoniophenolate is one represented by the following general formula (3):

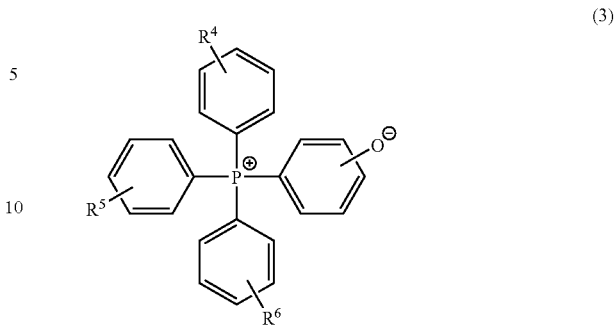
(3)

wherein $R^4$, $R^5$ and $R^6$ may be the same as or different from one another, and each is selected from a group consisting of a hydrogen atom, a methyl group, a methoxy group and a hydroxyl group.

In this case, in the general formula (3), the oxyanion is preferably located in ortho position or meta position to the phosphorus atom.

In the present invention, it is preferred that the salt of trisubstituted phosphoniophenolate is one represented by the following general formula (4):

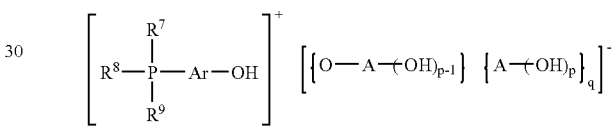
(4)

wherein $R^7$, $R^8$ and $R^9$ may be the same as or different from one another, and each represents a substituted or unsubstituted monovalent aromatic group or a substituted or unsubstituted monovalent alkyl group; Ar represents an unsubstituted divalent aromatic group or a divalent aromatic group in which at least one hydrogen atom is substituted with a substituent other than a hydroxyl group; A represents a p-valent organic group containing at least one aromatic ring and/or at least one heterocycle; and p is an integer of 2 to 8 and q is 0 to 2.

Further, it is also preferred that the salt of trisubstituted phosphoniophenolate is one represented by the following general formula (5):

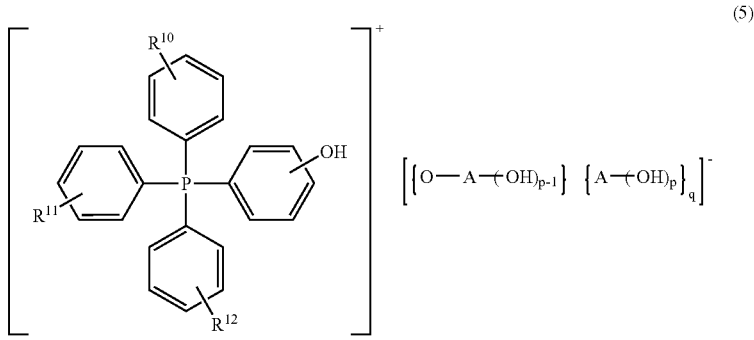
(5)

wherein $R^{10}$, $R^{11}$ and $R^{12}$ may be the same as or different from one another, and each is selected from a group consisting of a hydrogen atom, a methyl group, a methoxy group and a hydroxyl group; A represents a p-valent organic group containing at least one aromatic ring and/or at least one heterocycle; and p is an integer of 2 to 8 and q is 0 to 2.

Furthermore, it is also preferred that the salt of trisubstituted phosphoniophenolate is one represented by the following general formula (6) or (7):

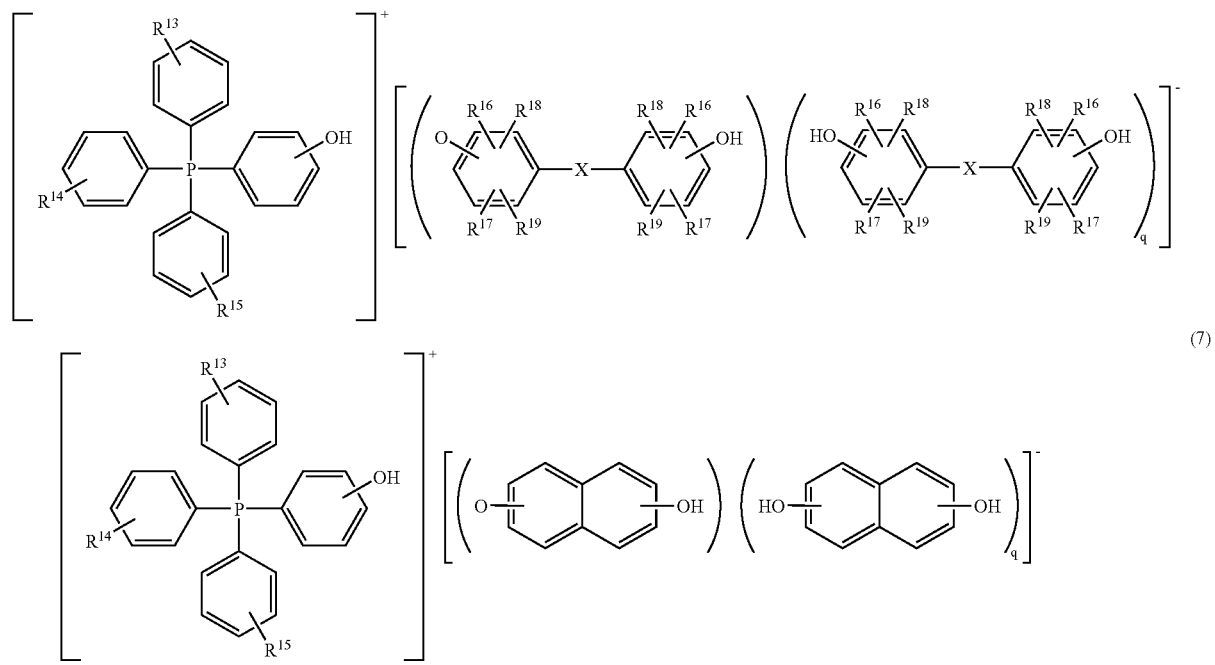

wherein $R^{13}$, $R^{14}$ and $R^{15}$ may be the same as or different from one another, and each is selected from a group consisting of a hydrogen atom, a methyl group, a methoxy group and a hydroxyl group; $R^{16}$, $R^{17}$, $R^{18}$ and $R^{19}$ may be the same as or different from one another, and each is selected from a group consisting of a hydrogen atom, a halogen atom and a monovalent organic group having 1 to 6 carbon atoms; X represents a single bond, an ether group, a sulfone group, a sulfide group, a carbonyl group or a divalent organic group having 1 to 13 carbon atoms; and q is 0 to 2.

In the salt of trisubstituted phosphoniophenolate described above, the hydroxyl group in the cation component is preferably located in ortho position or meta position to the phosphorus atom.

Another aspect of the present invention is directed to an epoxy resin composition comprising a compound having two or more epoxy groups in one molecule, a compound having two or more phenolic hydroxyl groups in one molecule, and the curing accelerator described above.

In the epoxy resin composition of the present invention, it is preferred that the compound having two or more epoxy groups in one molecule contains as a main ingredient at least one of epoxy resins represented by the following general formulas (8) and (9):

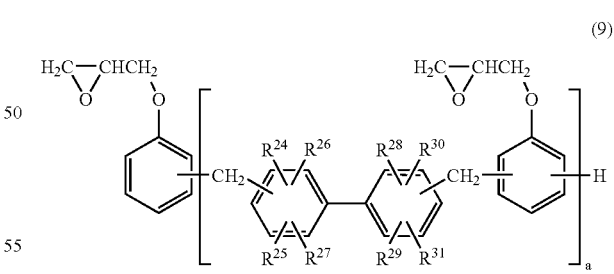

wherein $R^{20}$, $R^{21}$, $R^{22}$ and $R^{23}$ may be the same as or different from one another, and each is selected from a group consisting of a hydrogen atom, a linear or cyclic alkyl group having 1 to 6 carbon atoms, a phenyl group and a halogen atom; and wherein $R^{24}$ to $R^{31}$ may be the same as or different from one another, and each is selected from a group consisting of a hydrogen atom, an alkyl group having 1 to 4 carbon atoms and a halogen atom; and a is an integer of 1 or more.

In this case, a is preferably an integer of 1 to 10.

Further, it is also preferred that the compound having two or more phenolic hydroxyl groups in one molecule contains as a main ingredient at least one of phenolic resins represented by the following general formulas (10) and (11):

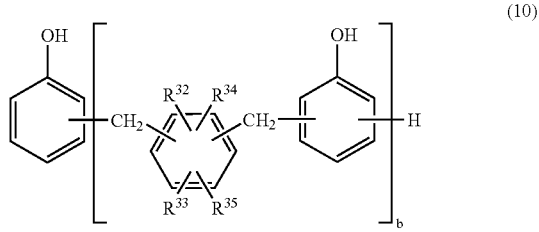

(10)

wherein $R^{32}$ to $R^{35}$ may be the same as or different from one another, and each is selected from a group consisting of a hydrogen atom, an alkyl group having 1 to 4 carbon atoms and a halogen atom; and b is an integer of 1 or more; and

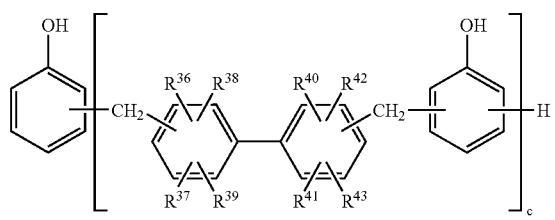

(11)

wherein $R^{36}$ to $R^{43}$ may be the same as or different from one another, and each is selected from a group consisting of a hydrogen atom, an alkyl group having 1 to 4 carbon atoms and a halogen atom; and c is an integer of 1 or more.

In this case, b is preferably an integer of 1 to 10, and c is preferably an integer of 1 to 10.

Furthermore, it is also preferred that the content of the curing accelerator is in the range of 0.01 to 10 wt %.

Moreover, it is also preferred that the epoxy resin composition further comprises an inorganic filler.

In this case, the inorganic filler is preferably fused silica.

Moreover, it is also preferred that the inorganic filler is in the form of granules or particles.

In this case, the average particle size of the inorganic filler is preferably in the range of 1 to 100 μm.

Moreover, it is also preferred that the content of the inorganic filler is in the range of 200 to 2,400 parts by weight per 100 parts by weight of the total amount of the compound having two or more epoxy groups in one molecule and the compound having two or more phenolic hydroxyl groups in one molecule.

Still another aspect of the present invention is directed to a semiconductor device manufactured by encapsulating at least one semiconductor element with a cured product of the epoxy resin composition described above.

DETAILED DESCRIPTION OF THE INVENTION

To solve the problems stated above, the present inventors have extensively studied, and as a result found the following facts (1) to (3). These findings have lead to completion of the present invention.

Specifically, (1) the fact that trisubstituted phosphoniophenolate having a specific structure or a salt thereof is extremely useful as a curing accelerator for promoting the curing reaction of various curable resin compositions has been found; (2) the fact that by mixing the trisubstituted phosphoniophenolate or the salt thereof as a curing accelerator into a curable resin composition, especially an epoxy resin composition, a resultant epoxy resin composition can have excellent curability, storage stability and fluidity has been found; and (3) the fact that even in a case where a semiconductor device manufactured by encapsulating a semiconductor element with a cured product of the epoxy resin composition is exposed to high temperature, defects such as cracking, delamination and the like are hard to occur has been found.

A description will now be made with regard to preferred embodiments of the curing accelerator, the epoxy resin composition and the semiconductor device of the present invention.

Although the curing accelerator of the present invention can be used as a curing accelerator for various curable resin compositions, the following description will be made based on the exemplary case where the curing accelerator is used for an epoxy rein composition which is a kind of thermosetting resin composition.

The epoxy resin composition of the present embodiment includes: a compound (A) having two or more epoxy groups in one molecule; a compound (B) having two or more phenolic hydroxyl groups in one molecule; trisubstituted phosphoniophenolate or a salt thereof (C) which is a curing accelerator of the present invention; and an inorganic filler (D). Such an epoxy resin composition has excellent curability, storage stability and fluidity.

Hereinbelow, each of the components will be described in order.

<Compound (A)>

The compound (A) has two or more epoxy groups in one molecule, and there is no restraint on the compound (A) as long as it has two or more epoxy groups in one molecule.

Examples of the compound (A) include: epoxy resins obtained by reacting hydroxyl groups in phenols, phenolic resins or naphthols and epichlorohydrin, such as bisphenol type epoxy resin e.g., bisphenol A type epoxy resin, bisphenol F type epoxy resin or brominated bisphenol type epoxy resin, stilbene type epoxy resin, phenol novolak type epoxy resin, cresol novolak type epoxy resin, naphthalene type epoxy resin, dicyclopentadiene type epoxy resin or dihydroxy benzene type epoxy resin; epoxy compounds; epoxy resins obtained by oxidizing olefins using peracid for epoxidation, such as cycloaliphatic epoxy resin; glycidyl ester type epoxy resin; and glycidyl amine type epoxy resin, and they can be used alone or in combination of two or more.

Among them, the compound (A) preferably contains as a main ingredient one or both of biphenyl type epoxy resin represented by the general formula (8) and biphenyl aralkyl type epoxy resin represented by the general formula (9). When such a compound (A) is contained in the epoxy resin composition, the epoxy resin composition exhibits excellent fluidity during molding (e.g., during manufacture of semiconductor devices). In addition, a semiconductor device manufactured using such an epoxy resin composition can have further improved solder cracking resistance.

In this regard, it is to be noted here that "improvement in solder cracking resistance" means that even in a case where an obtained semiconductor device is exposed to high temperature when it is immersed in solder or subjected to the reflow soldering process or the like, defects such as cracking, delamination and the like are hard to occur.

(8)

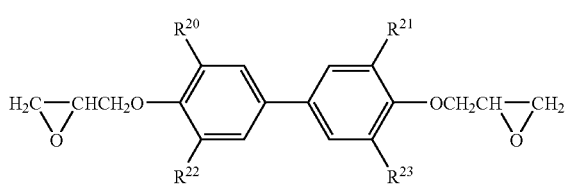

-continued

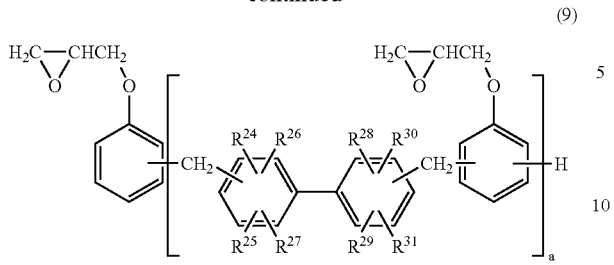
(9)

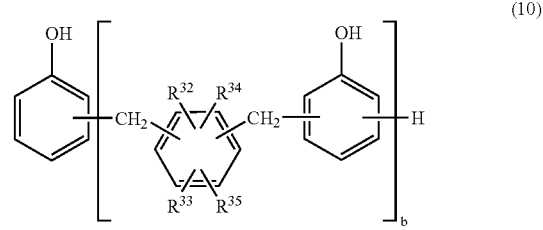
(10)

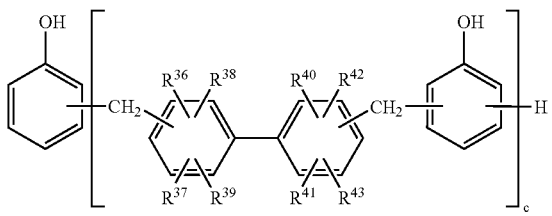
(11)

The substituents $R^{20}$ to $R^{23}$ in biphenyl type epoxy resin represented by the general formula (8) may be the same as or different from one another, and specific examples of these substituents include: a methyl group, an ethyl group, a propyl group, a butyl group, a chlorine atom and a bromine atom. Among them, a methyl group is particularly preferable. When at least one of the substituents $R^{20}$ to $R^{23}$ is a methyl group, the melt viscosity of the epoxy resin composition is decreased, and therefore handling of the epoxy resin composition becomes easy in, for example, manufacturing semiconductor devices. Further, a cured product of the epoxy resin composition has reduced moisture absorption so that it is possible to effectively prevent deterioration with age of parts (e.g., occurrence of breakage of wires) in an obtained semiconductor device. Therefore, the moisture resistance reliability of the obtained semiconductor device is further improved.

The substituents $R^{24}$ to $R^{31}$ in biphenyl aralkyl type epoxy resin represented by the general formula (9) may be the same as or different from one another, and specific examples of these substituents include: a hydrogen atom, a methyl group, an ethyl group, a propyl group, a butyl group, a chlorine atom and a bromine atom. Among them, a hydrogen atom or a methyl group is particularly preferable. When at least one of the substituents $R^{24}$ to $R^{31}$ is a hydrogen atom or a methyl group, the melt viscosity of the epoxy resin composition is decreased, and therefore handling of the epoxy resin composition becomes easy in, for example, manufacturing semiconductor devices. In addition, the moisture resistance reliability of an obtained semiconductor device is further improved.

It is to be noted that a in the general formula (9) indicates an average number of times that epoxy resin unit is repeated. Specifically, a is not limited to any specific value as long as it is an integer of 1 or more, but is preferably in the range of about 1 to 10, and more preferably in the range of about 1 to 5. By setting the value of a to the above range, the fluidity of the epoxy resin composition is further improved.

<Compound (B)>

The compound (B) has two or more phenolic hydroxyl groups in one molecule, and acts (functions) as a curing agent for the compound (A) described above.

Examples of the compound (B) include phenol novolak resin, cresol novolak resin, bisphenol resin, trisphenol resin, xylylene-modified novolak resin, terpene-modified novolak resin and dicyclopentadiene-modified phenolic resin. They can be used alone or in combination of two or more.

Among them, the compound (B) preferably contains as a main ingredient one or both of phenol aralkyl resin represented by the general formula (10) and biphenyl aralkyl type phenolic resin represented by the general formula (11). When such a compound (B) is contained in the epoxy resin composition, the epoxy resin composition exhibits excellent fluidity during molding (e.g., during manufacture of semiconductor devices) In addition, a semiconductor device manufactured using such an epoxy resin composition can have further improved solder cracking resistance and moisture resistance reliability.

The substituents $R^{32}$ to $R^{35}$ in phenol aralkyl resin represented by the general formula (10) may be the same as or different from one another, and the substituents $R^{36}$ to $R^{43}$ in biphenyl aralkyl type phenolic resin represented by the general formula (11) may also be the same as or different from one another. Specific examples of these substituents include a hydrogen atom, a methyl group, an ethyl group, a propyl group, a butyl group, a chlorine atom, and a bromine atom. Among them, a hydrogen atom or a methyl group is particularly preferable. Such a phenolic resin itself has low melt viscosity so that even in a case where the phenolic resin is contained in the epoxy resin composition, it is possible to keep the melt viscosity of the epoxy resin composition low. As a result, handling of the epoxy resin composition becomes easy during, for example, manufacture of semiconductor devices. In addition, a cured product of the epoxy resin composition has reduced water absorption (moisture absorption) so that the moisture resistance reliability and the solder cracking resistance of an obtained semiconductor device are further improved.

Further, it is to be noted here that b in the general formula (10) and c in the general formula (11) respectively indicate an average number of times that phenolic resin unit is repeated. Specifically, each of b and c is not limited to any specific value as long as it is an integer of 1 or more, but is preferably in the range of about 1 to 10, and more preferably in the range of about 1 to 5. By setting the value of each of b and c to the above range, it is possible to prevent or suppress a lowering in the fluidity of the epoxy resin composition.

<Trisubstituted Phosphoniophenolate or Salt Thereof (C): Curing Accelerator of the Present Invention>

The trisubstituted phosphoniophenolate or the salt thereof (C) is one having the effect (function) of promoting the curing reaction of the epoxy resin composition. As for the trisubstituted phosphoniophenolate (phosphonium inner salt), one represented by the general formula (1) is preferable, one represented by the general formula (2) is more preferable, and one represented by the general formula (3) is even more preferable.

(1)

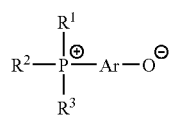

-continued $$Ar^2-\overset{Ar^1}{\underset{Ar^3}{\overset{|}{P}^{\oplus}}}-Ar-O^{\ominus} \quad (2)$$

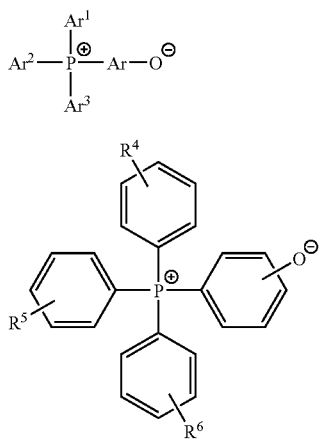
(3)

In the general formula (1), the substituents $R^1$, $R^2$ and $R^3$ bonded to the phosphorus atom may be the same as or different from one another, and specific examples of these substituents include a benzyl group, a methyl group, an ethyl group, an n-butyl group, an n-octyl group, and a cyclohexyl group. Preferably, each of the substituents $R^1$ to $R^3$ is a substituted or unsubstituted monovalent aromatic group such as a naphthyl group, a p-tertiary-butylphenyl group or a 2,6-dimethoxyphenyl group, as respectively represented by $Ar^1$, $Ar^2$ and $Ar^3$ in the general formula (2), and is more preferably a phenyl group, one of the isomers of a methylphenyl group, one of the isomers of a methoxyphenyl group or one of the isomers of a hydroxyphenyl group, as represented by the general formula (3).

In the general formulas (1) and (2), each Ar represents an unsubstituted divalent aromatic group or a divalent aromatic group in which at least one hydrogen atom is substituted with a substituent other than a hydroxyl group.

Specific examples of the substituent Ar include aromatic groups such as a phenylene group, a biphenylene group, a naphthylene group and each of them in which at least one hydrogen atom is substituted with a substituent other than a hydroxyl group, such as a halogen atom, a nitro group, a cyano group, or an alkyl or alkoxy group having 1 to 12 carbon atoms.

More specifically, as for the substituents $R^1$, $R^2$, $R^3$ and Ar in the general formula (1), it is preferable that each of the substituents $R^1$, $R^2$ and $R^3$ is a phenyl group and the substituent Ar is a phenylene group. That is, trisubstituted phosphoniophenolate represented by the general formula (3) in which each of the substituents $R^4$, $R^5$ and $R^6$ is a hydrogen atom is preferable. Such trisubstituted phosphoniophenolate has especially excellent heat stability and effect of promoting curing reaction, and can be produced at low cost.

Further, trisubstituted phosphoniophenolate represented by the general formula (3) in which the oxyanion (dissociated from a phenolic hydroxyl group) is located in ortho position or meta position to the phosphorus atom is preferable. When the epoxy resin composition contains as a curing accelerator such trisubstituted phosphoniophenolate in which the oxyanion is located in ortho or meta position to the phosphorus atom, modulus of elasticity of the epoxy resin composition during heating is further reduced, as compared with the case where trisubstituted phosphoniophenolate in which the oxyanion is located in para position to the phosphorus atom is used as a curing accelerator. Further, by encapsulating semiconductor elements with such an epoxy resin composition having reduced modulus of elasticity, an obtained semiconductor device can have improved solder cracking resistance.

On the other hand, as for the salt of trisubstituted phosphoniophenolate (phosphonium molecular compound), one represented by the general formula (4) is preferable, one represented by the general formula (5) is more preferable, and one represented by the general formula (6) or (7) is even more preferable.

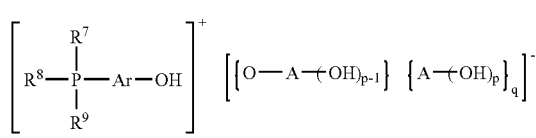
(4)

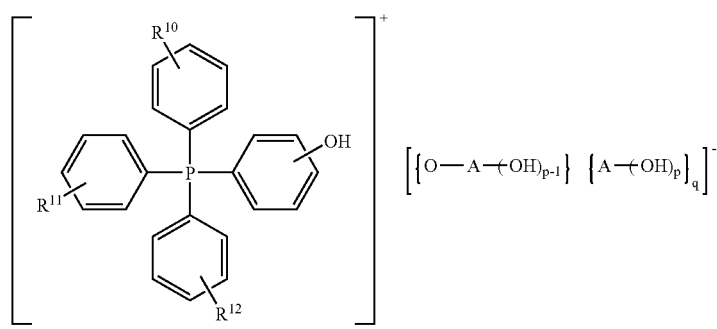
(5)

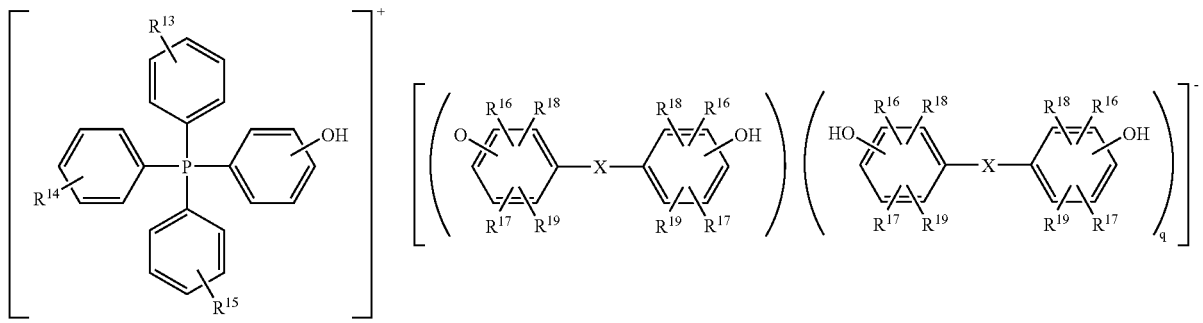

(6)

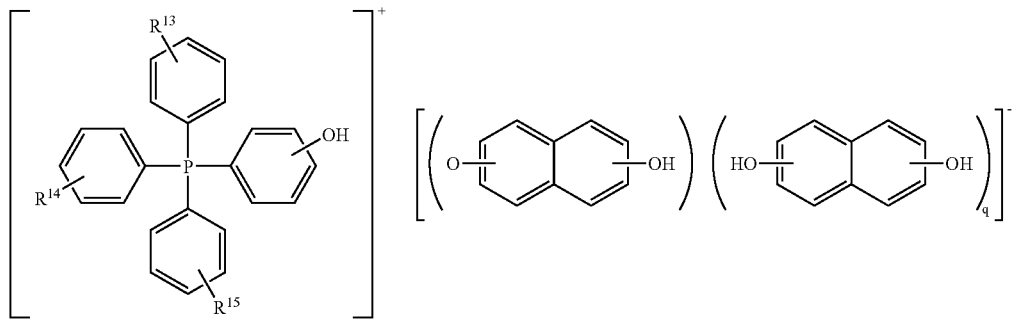

(7)

The substituents $R^7$, $R^8$ and $R^9$ which are bonded to the phosphorus atom in the general formula (4) may be the same as or different from one another, and specific examples of these substituents include a benzyl group, a methyl group, an ethyl group, an n-butyl group, an n-octyl group, and a cyclohexyl group. Preferably, each of the substituents $R^7$, $R^8$ and $R^9$ is a substituted or unsubstituted monovalent aromatic group such as a naphthyl group, a p-tertiary-butylphenyl group or a 2,6-dimethoxyphenyl group, and is more preferably a phenyl group, one of the isomers of a methylphenyl group, one of the isomers of a methoxyphenyl group or one of the isomers of a hydroxyphenyl group, as shown in the general formulas (5) to (7).

Further, in the general formula (4), the substituent Ar represents an unsubstituted divalent aromatic group or a divalent aromatic group in which at least one hydrogen atom is substituted with a substituent other than a hydroxyl group.

Specific examples of the substituent Ar include aromatic groups such as a phenylene group, a biphenylene group, a naphthylene group, and each of them in which at least one hydrogen atom is substituted with a substituent other than a hydroxyl group, such as a halogen atom, a nitro group, a cyano group, or an alkyl or alkoxy group having 1 to 12 carbon atoms.

More specifically, as for the substituents $R^7$, $R^8$ and $R^9$ and Ar in the general formula (4), it is preferable that each of the substituents $R^7$, $R^8$ and $R^9$ is a phenyl group, and the substituent Ar is a phenylene group. That is, a salt of trisubstituted phosphoniophenolate represented by the general formula (5) in which each of the $R^{10}$ to $R^{12}$ is a hydrogen atom, or a salt of trisubstituted phosphoniophenolate represented by the general formula (6) or (7) in which each of the $R^{13}$ to $R^{15}$ is a hydrogen atom is preferable. Such a salt of trisubstituted phosphoniophenolate has especially excellent heat stability and effect of promoting curing reaction, and can be produced at low cost.

Further, a salt of trisubstituted phosphoniophenolate in which the hydroxyl group (phenolic hydroxyl group) in the cation component thereof is located in ortho position or meta position to the phosphorus atom is preferable. When the epoxy resin composition contains as a curing accelerator such a salt of trisubstituted phosphoniophenolate in which the hydroxyl group is located in ortho or meta position to the phosphorus atom, modulus of elasticity of the epoxy resin composition during heating is further reduced, as compared with the case where a salt of trisubstituted phosphoniophenolate in which the hydroxyl group is located in para position to the phosphorus atom is used as a curing accelerator. Further, by encapsulating semiconductor elements with such an epoxy resin composition having reduced modulus of elasticity, an obtained semiconductor device can have improved solder cracking resistance.

In the general formulas (4) to (7), various phenol compounds (phenol based compounds) can be suitably used as the anion component forming the salt of trisubstituted phosphoniophenolate. Examples of such a phenol compound include: bisphenols such as bisphenol A (2,2-bis(4-hydroxyphenyl)propane), bisphenol F (4,4-methylenebisphenol, 2,4-methylenebisphenol, 2,2-methylenebisphenol), bisphenol S (2,2-bis(4-hydroxyphenyl)sulfone), bisphenol E (4,4-ethylidenebisphenol), bisphenolfluorene (4,4-(9H-fluorene-9-ylidene)bisphenol), 4,4-methylidenebis(2,6-dimethylphenol) or bis(4-hydroxyphenyl)methanone; biphenols such as 4,4-biphenol, 2,2-biphenol or 3,3,5,5-tetramethylbiphenol; hydroquinone; resorcinol; catechol; 2,6-dihydroxynaphthalene; 1,4-dihydroxynaphthalene; 2,3-dihydroxynaphthalene; 1,6-dihydroxynaphthalene; 1,1-bi-2-naphthol; 1,4-dihydroxyanthraquinone; pyrogallol; and phloroglucinol.

Among them, divalent phenol compounds are preferable as shown in the general formulas (4) and (5) in which p is 2, and divalent phenol compounds shown in the general formulas (6) and (7) are also preferable. Further, divalent phenol compounds shown in the general formulas (4) and (5) in which p is 2 and q is 0.5 to 2, and divalent phenol compounds shown in the general formulas (6) and (7) in which q is 0.5 to 2 are more preferable. Specifically, bisphenol A, bisphenol F (4,4-methylenebisphenol, 2,4-methylenebisphenol, 2,2-methylenebisphenol or bisphenol F-D made by HONSHU CHEMICAL INDUSTRY CO., LTD., which is a mixture of these isomers of bisphenol F), bisphenol S, 4,4-biphenol, 2,3-dihydroxynaphthalene and 1,6-dihydroxynaphthalene are more preferable. By using a salt of trisubstituted phosphoniophenolate, which contains such a phenol compound as the anion component, for a curable resin composition as a curing accelerator, the curable resin composition can have excellent fluidity, and as a result a cured product thereof has especially excellent physical properties.

In this regard, it is to be noted that the salt of trisubstituted phosphoniophenolate to be used in the present invention may be formed as a molecular compound, a clathrate compound, a complex compound or the like, instead of an ionic compound composed of a cation part and an anion part as usual.

In the epoxy resin composition of the present invention, the content (blending amount) of the trisubstituted phosphoniophenolate or the salt thereof (C) is not limited to any specific value, but is preferably in the range of about 0.01 to 10 wt %, more preferably in the range of about 0.1 to 5 wt %, and most preferably in the range of about 0.1 to 1 wt %. By setting the content of the trisubstituted phosphoniophenolate or the salt thereof to the above range, it is possible to provide an epoxy resin composition having an excellent balance of curability, storage stability, fluidity and other properties.

The blending ratio of the compound (A) to the compound (B) is not limited to any specific value, but they are preferably blended such that about 0.5 to 2 mol, more preferably about 0.7 to 1.5 mol of phenolic hydroxyl group in the compound (B) is available per 1 mol of epoxy group in the compound (A). This makes it possible to further improve various properties of the epoxy resin composition while keeping an excellent balance of the properties.

Hereinbelow, a description will be made with regard to an example of a method for producing the trisubstituted phosphoniophenolate or the salt thereof which is a curing accelerator of the present invention, with reference to the following equation (12):

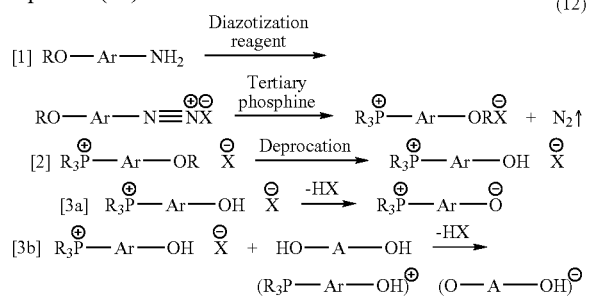

(12)

wherein R represents a hydrogen atom or a residue appropriately selected, and X represents a halogen atom.

(Process 1)

First, for example, alkoxy-substituted aromatic amine is reacted with a diazotization reagent such as sodium nitrite under acid conditions to form a diazonium salt. Examples of the alkoxy-substituted aromatic amine to be used include o-methoxyaniline, m-methoxyaniline, p-methoxyaniline, 2-methoxy-5-methylaniline and the like.

Next, the obtained diazonium salt is brought into contact with tertiary phosphines. By doing so, $N_2$ is eliminated and the alkoxy-substituted aromatic group is bonded to the phosphorus atom in the tertiary phosphine to generate a quaternary phosphonium salt. Namely, in the process (1), substitution of the diazonium group in the diazonium salt for the tertiary phosphine occurs. Examples of the tertiary phosphines to be used include triphenylphosphine, tri-p-tolylphosphine, tri(4-methoxyphenyl)phosphine and the like.

Such substitution reaction is preferably performed in the presence of alkali. By doing so, the substitution reaction efficiently proceeds. The alkali which is used in the reaction is not limited to a specific one, and examples of the alkali include: inorganic base such as sodium hydroxide, potassium hydroxide, calcium hydroxide, sodium carbonate, potassium carbonate, sodium hydrogen carbonate, sodium hydride, lithium hydride, calcium hydride or lithium aluminum hydride; and organic base such as triethylamine, tripropylamine, tributylamine, pyridine, piperidine, diaminoethane, diaminopropane, diaminobutane, diaminopentane, diaminohexane, diaminooctane or triethanolamine. These alkalis can be used alone or in combination of two or more.

A reaction temperature in the substitution reaction is not limited to any specific value, but is preferably in the range of about −10 to 10° C., and more preferably in the range of about 0 to 5° C. If the reaction temperature is too low, there is a case that the substitution reaction does not sufficiently proceed. On the other hand, if the reaction temperature is too high, there is a case that the tertiary phosphine and the diazonium salt are decomposed depending on the kinds thereof.

A reaction time in the substitution reaction is appropriately set depending on the kinds of tertiary phosphine and diazonium salt, and is not limited to a specific value, but is preferably in the range of about 20 to 120 minutes, and more preferably in the range of about 40 to 80 minutes. If the reaction time is too short, there is a case that the substitution reaction does not sufficiently proceed. On the other hand, even if the reaction time is lengthened so as to exceed the above upper limit value, an increase in yield can not be expected.

(Process 2)

Next, the alkoxy group is replaced by a hydroxyl group by a common deprotection method to obtain a hydrogen halide salt of trisubstituted phosphoniophenolate. In this way, a salt of trisubstituted phophoniophenolate can be easily obtained through these processes. However, in a case where trisubstituted phosphoniophenolate itself is to be prepared or a salt of trisubstituted phosphoniophenolate can be easily obtained through contact with acid, it is possible to utilize a reaction in which RX is directly eliminated, instead of the process 2.

(Processes 3a and 3b)

Next, the obtained hydrogen halide salt of trisubstituted phosphoniophenolate is neutralized in the absence of a phenolic component (process 3a) or in the presence of a phenolic component (process 3b) to synthesize trisubstituted phosphoniophenolate or a salt of trisubstituted phosphoniophenolate, respectively. It is to be understood that the method for producing the curing accelerator of the present invention is not limited to these processes.

As a common example of trisubstituted phosphoniophenolate, a compound which can be obtained by addition reaction of tertiary phosphine with quinones is known. As for the most representative trisubstituted phosphoniophenolate, an adduct of tertiary phosphine with p-benzoquinone, which is represented by the formula (13) can be mentioned.

(13)

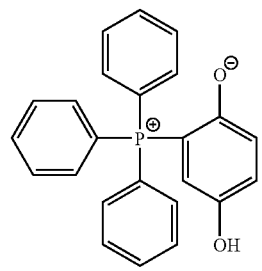

Such trisubstituted phosphoniophenolate has a feature that a hydroxyl group is located in para position to the oxyanion, and the structure thereof is completely different from that of the trisubstituted phophoniophenolate used in the present invention (the curing accelerator of the present invention).

Such a structural feature is common to trisubstituted phosphoniophenolate which is obtained as an adduct of tertiary phosphine with quinones ("quinone is a compound having a structure in which two hydrogen atoms bonded to a benzene ring of an aromatic hydrocarbon are replaced by two oxygen atoms", which is cited from "Kagaku Daijiten" published by KYORITU SHUPPAN CO., LTD.). That is, two carbonyl groups in the quinone are respectively converted into an oxyanion and a hydroxyl group in a resultant phosphoniophenolate.

Therefore, the trisubstituted phosphoniophenolate used in the present invention, which does not have a hydroxyl group located in para position to the oxyanion, can not be obtained by addition reaction of tertiary phosphine with quinones.

Further, the trisubstituted phosphoniophenolate or the salt thereof (C) which is the curing accelerator of the present invention has extremely excellent properties as a curing accelerator, especially storage stability, as compared with an adduct of tertiary phosphine with p-benzoquinone (which is a compound represented by the formula (13) and is a conventional curing accelerator). The reason for this is considered that the bonding of an ion pair between a phosphonium cation and an oxyanion in a molecule is extremely stable in room temperature. On the other hand, in a case where a hydroxyl group is located in para position to an oxyanion as is the case with the adduct of tertiary phosphine with p-benzoquinone (that is a compound represented by the formula (13)), it is considered that the state of charge of the oxyanion is unstable so that a stable ion pair in a molecule is hard to be formed.

<Inorganic Filler (D)>

The inorganic filler (D) is blended (mixed) into the epoxy resin composition for the purpose of reinforcing an obtained semiconductor device. Such an inorganic filler is not particularly limited, and one which is commonly used for an encapsulating material can be used.

Examples of the inorganic filler (D) include crushed fused silica, fused silica, crystalline silica, secondary agglomerated silica, alumina, titanium white, aluminum hydroxide, talc, clay, glass fiber and the like, and these fillers can be used alone or in combination of two or more. Among them, fused silica is particularly preferable as the inorganic filler (D). Since fused silica has poor reactivity with the curing accelerator of the present invention, even in a case where such fused silica is blended (mixed) into the epoxy resin composition in large quantity as will be described later, the curing reaction of the epoxy resin composition is not interfered. Further, by using such fused silica as the inorganic filler (D), the effect of reinforcing an obtained semiconductor device is improved.

Further, the shape of the inorganic filler (D) is not particularly limited, and may be granule, agglomerate, flake or the like. Among them, an inorganic filler in the form of granules or particles (especially, spherical particles) is preferably used as the inorganic filler (D).

When an inorganic filler in the form of granules or particles is used, the average particle size of the inorganic filler (D) is preferably in the range of about 1 to 100 µm, and more preferably in the range of about 5 to 35 µm. In addition, the inorganic filler preferably has a wide size distribution. By using such an inorganic filler as the inorganic filler (D), it is possible to fill (use) the inorganic filler in large quantity and as a result, the effect of reinforcing an obtained semiconductor device is improved.

The content (blending amount) of the inorganic filler (D) is not limited to any specific value, but is preferably in the range of about 200 to 2,400 parts by weight per 100 parts by weight of the total weight of the compound (A) and the compound (B), and more preferably in the range of about 400 to 1,400 parts by weight. If the content of the inorganic filler (D) is less than the above lower limit value, there is a case that the reinforcing effect by the addition of the inorganic filler is not sufficiently developed in an obtained semiconductor device. On the other hand, if the content of the inorganic filler (D) exceeds the above upper limit value, a resultant epoxy resin composition has lowered fluidity, thus resulting in the case that short shot or the like occurs during molding of the epoxy resin composition (e.g., during manufacture of semiconductor devices).

When the content (blending amount) of the inorganic filler (D) is within the range of 400 to 1,400 parts by weight per 100 parts by weight of the total weight of the compound (A) and the compound (B), a cured product of the epoxy resin composition has reduced moisture absorption so that solder cracking is prevented from occurring in an obtained semiconductor device. Further, since such an epoxy resin composition exhibits excellent fluidity during molding by heating, it is possible to effectively prevent gold wires from being deformed in a semiconductor device.

It is to be noted that the content (blending amount) of the inorganic filler (D) may be determined by using a value represented by volume percent instead of parts by weight in consideration of the specific gravity of each of the compound (A), the compound (B) and the inorganic filler (D).

If necessary, various additives such as a coupling agent e.g., γ-glycidoxypropyltrimethoxysilane, a coloring agent e.g., carbon black, a flame retardant e.g., brominated epoxy resin, antimony oxide or phosphorus compound, a low-stress component e.g., silicone oil or silicone rubber, a releasing agent e.g., natural wax, synthetic wax, higher fatty acid or metal salts thereof, or paraffin, an antioxidant and the like may be blended (mixed) into the epoxy resin composition of the present invention in addition to the compounds (components) (A) to (D).

There is no problem in blending (mixing) other known catalysts such as triphenyl phosphine, 1,8-diazabicyclo(5,4, 0)-undecene-7 and 2-methylimidazole into the epoxy resin composition within the range not impairing the capability of the trisubstituted phosphoniophenolate or the salt thereof (C) as the curing accelerator of the present invention.

The epoxy resin composition of the present invention can be obtained through the processes of mixing of the compounds (components) (A) to (D) and other optional additives using a mixer at room temperature, kneading of the mixture using a hot roll or a heated kneader, and cooling and then grinding of the mixture.

The thus obtained epoxy resin composition for use as a mold resin is molded and cured by a molding method such as transfer molding, compression molding, injection molding or the like to encapsulate an electronic part such as a semiconductor element. In this way, a semiconductor device of the present invention can be obtained.

The type of the semiconductor device of the present invention is not limited to any specific one, and examples of the semiconductor device include SIP (Single Inline Package), HSIP (SIP with Heatsink), ZIP (Zig-zag Inline Package), DIP (Dual Inline Package), SDIP (Shrink Dual Inline Package), SOP (Small Outline Package), SSOP (Shrink Small Outline Package), TSOP (Thin Small Outline Package), SOJ (Small Outline J-leaded Package), QFP (Quad Flat Package), QFP (FP) (QFP Fine Pitch), TQFP (Thin Quad Flat Package), QFJ (PLCC) (Quad Flat J-leaded Package) and BGA (Ball Grid Array).

The semiconductor device of the present invention obtained in such a manner described above has excellent solder cracking resistance and moisture resistance reliability. The reason for this is considered that the trisubstituted phosphoniophenolate or the salt thereof (C) which is the curing accelerator of the present invention is stable in the soldering process (e.g., reflow soldering process or the like).

If an adduct of tertiary phosphine with quinones (e.g., a compound represented by the formula (13)) is used as a curing accelerator for an epoxy resin composition (thermosetting resin composition), a reverse reaction of addition reaction occurs at a certain rate when a cured product of the epoxy resin composition is exposed to high temperature in the reflow soldering process, for example, and as a result, decomposition of the adduct into tertiary phosphine and quinones occurs.

At this time, the tertiary phosphine and the quinines, or compounds (components) generated by the reaction between other components contained in the epoxy resin composition (cured product) and the tertiary phosophine and quinones may be volatilized, thus resulting in the case where cracking occurs.

On the other hand, since the trisubstituted phosphoniophenolate or the salt thereof (C) which is the curing accelerator of the present invention is synthesized by substitution reaction as described above, higher energy is required to initiate a reverse reaction (decomposition of the compound) as compared with the case of the adduct. For this reason, the possibility that the curing accelerator of the present invention is decomposed in general soldering conditions is extremely low.

Therefore, the semiconductor device of the present invention has excellent solder cracking resistance and moisture resistance reliability as compared with a semiconductor device which is encapsulated with a cured product of an epoxy resin composition containing the adduct of tertiary phosphine with quinones (e.g., a compound represented by the formula (13)) as a curing accelerator.

In this regard, it is to be noted that a description has been made based on the exemplary case where the curing accelerator (that is the trisubstituted phosphoniophenolate or the salt thereof represented by any one of the general formulas (1) to (7)) of the present invention is used for the epoxy resin composition, but the curing accelerator of the present invention can be used for thermosetting resin compositions for which phosphine or phosphonium salt can be suitably used as a curing accelerator. Examples of such a thermosetting resin composition include resin compositions containing epoxy compounds, maleimide compounds, cyanate compounds, isocyanate compounds, acrylate compounds, or alkenyl and alkynyl compounds, or the like.

The curing accelerator of the present invention can be used for various curable resin compositions such as reactive curable resin compositions, photo-curable resin compositions or anaerobic curable resin compositions, in addition to thermosetting resin compositions.

In the present embodiment, although a description has been made based on the case where the epoxy resin composition of the present invention is used as an semiconductor encapsulating material, the use of the epoxy resin composition of the present invention is not limited thereto. In the epoxy resin composition of the present invention, mixing (blending) of the inorganic filler may be omitted according to the use of the epoxy resin composition.

Although the preferred embodiments of the curing accelerator, the epoxy resin composition, and the semiconductor device of the present invention have been described, the present invention is not limited to these embodiments.

EXAMPLE

Next, actual examples of the present invention will be described.

1. Evaluation of Trisubstituted Phosphoniophenolates

First, compounds C1 to C10 and triphenylphosphine were prepared as a curing accelerator.

1-1 Synthesis of Curing Accelerator

Each of the compounds C1 to C10 was synthesized as follows.

(Synthesis of Compound C1)

12.3 g of o-methoxyaniline (0.100 mol) and an aqueous hydrochloric acid solution, which had been prepared by dissolving 25 ml of concentrated hydrochloric acid (37%) in 200 ml of pure water in advance, were put into a 500 ml separable flask equipped with a condenser and a stirrer, and they were stirred to dissolve o-methoxyaniline.

Thereafter, the separable flask was cooled with ice such that the temperature in the flask was held at 0 to 5° C., and in this state 7.2 g (0.104 mol) of sodium nitrite dissolved in 20 ml of pure water was slowly dropped into the solution in the flask.

Then, 20.0 g (0.076 mol) of triphenylphosphine dissolved in 150 ml of ethyl acetate was dropped into the separable flask and then the solution in the flask was stirred for 20 minutes.

Then, 8.0 g (0.200 mol) of sodium hydroxide dissolved in 20 ml of pure water was slowly dropped into the separable flask, and then the solution in the flask was strongly stirred for about 1 hour.

After bubbling of nitrogen gas was very slight, dilute hydrochloric acid was added until pH reached 3.0 or below, and 30 g (0.200 mol) of sodium iodide was then added. A resultant precipitate was filtered and then dried to obtain 29.7 g of reddish brown crystal of 2-methoxyphenyl triphenylphosphonium iodide.

Next, 29.7 g (0.060 mol) of the obtained 2-methoxyphenyl triphenylphosphonium iodide, 88.7 g (0.769 mol) of pyridine hydrochloride, and 12.0 g (0.118 mol) of acetic anhydride were put into a 500 ml separable flask equipped with a condenser and a stirrer, and they were heated at 200° C. for 5 hours under reflux and stirring.

After reaction was completed, a reaction product was cooled to room temperature, and then 3.3 g (0.022 mol) of sodium iodide dissolved in 250 ml of pure water was put into the separable flask. A precipitated solid was filtered and then dried to obtain 24.1 g of a brown solid of 2-hydroxyphenyl triphenylphosphonium iodide.

Next, 24.1 g (0.050 mol) of the thus obtained 2-hydroxyphenyl triphenylphosphonium iodide and 100 ml of methanol were put into a 500 ml separable flask equipped with a condenser and a stirrer and they were stirred to dissolve 2-hydroxyphenyl triphenylphosphonium iodide. Then, 125 ml of a 10% aqueous sodium hydrogen carbonate solution was slowly dropped into the flask under stirring.

After bubbling of carbon dioxide gas was very slight, the solution in the flask was heated at around 70° C. for about 2 minutes, and then was cooled. A precipitated crystal was filtered and then dried to obtain 15.9 g of yellowish brown crystal.

The thus obtained crystal was defined as a compound C1. As a result of analyses of the compound C1 by $^1$H-NMR, mass spectrometry, and elementary analysis, it was confirmed that the compound C1 was a target trisubstituted phosphoniophenolate represented by the following formula (14). The yield of the compound C1 was 59%.

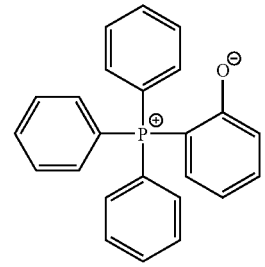

(14)

(Synthesis of Compound C2)

A compound was synthesized in the same manner as the compound C1 except that 12.3 g (0.100 mol) of m-methoxyanililne was used instead of o-methoxyaniline, to thereby ultimately obtain 12.0 g of yellow crystal.

The thus obtained crystal was defined as a compound C2. As a result of analyses of the compound C2 by $^1$H-NMR, mass spectrometry, and elementary analysis, it was confirmed that the compound C2 was a target trisubstituted phosphoniophenolate represented by the following formula (15). The yield of the compound C2 was 45%.

(15)

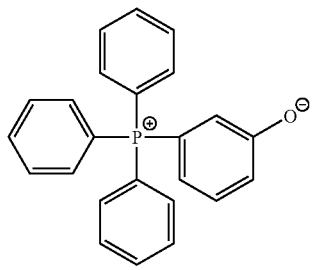

(Synthesis of Compound C3)

A compound was synthesized in the same manner as the compound C1 except that 12.3 g (0.100 mol) of p-methoxyaniline was used instead of o-methoxyaniline, to thereby ultimately obtain 17.5 g of pale yellow crystal.

The thus obtained crystal was defined as a compound C3. As a result of analyses of the compound C3 by $^1$H-NMR, mass spectrometry, and elementary analysis, it was confirmed that the compound C3 was a target trisubstituted phosphoniophenolate represented by the following formula (16). The yield of the compound C3 was 65%.

(16)

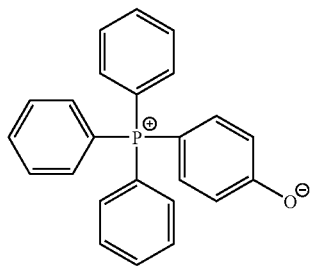

(Synthesis of Compound C4)

A compound was synthesized in the same manner as the compound C1 except that 13.7 g (0.100 mol) of 2-methoxy-5-methylaniline was used instead of o-methoxyaniline and that 23.1 g (0.076 mol) of tri-p-tolylphosphine was used instead of triphenylphosphine, to thereby ultimately obtain 17.0 g of brown crystal.

The thus obtained crystal was defined as a compound C4. As a result of analyses of the compound C4 by $^1$H-NMR, mass spectrometry, and elementary analysis, it was confirmed that the compound C4 was a target trisubstituted phosphoniophenolate represented by the following formula (17). The yield of the compound C4 was 55%.

(17)

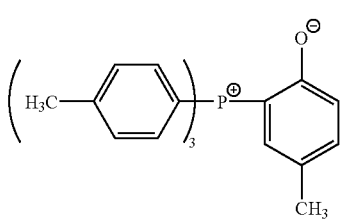

(Synthesis of Compound C5)

A compound was synthesized in the same manner as the compound C1 except that 26.8 g (0.076 mol) of tris(4-methoxyphenyl)phosphine was used instead of triphenylphosphine, to thereby ultimately obtain 16.5 g of pale yellowish white crystal.

The thus obtained crystal was defined as a compound C5. As a result of analyses of the compound C5 by $^1$H-NMR, mass spectrometry, and elementary analysis, it was confirmed that the compound C5 was a target trisubstituted phosphoniophenolate represented by the following formula (18). The yield of the compound C5 was 54%.

(18)

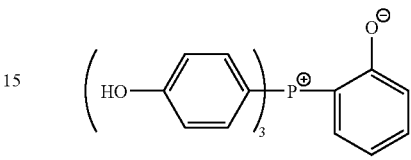

(Synthesis of Compound C6)

A compound was synthesized in the same manner as the compound C1 except that 19.9 g (0.100 mol) of 5-phenyl-2-methoxyaniline was used instead of o-methoxyaniline, to thereby ultimately obtain 23.5 g of yellow crystal.

The thus obtained crystal was defined as a compound C6. As a result of analyses of the compound C6 by $^1$H-NMR, mass spectrometry, and elementary analysis, it was confirmed that the compound C6 was a target trisubstituted phosphoniophenolate represented by the following formula (19). The yield of the compound C6 was 72%.

(19)

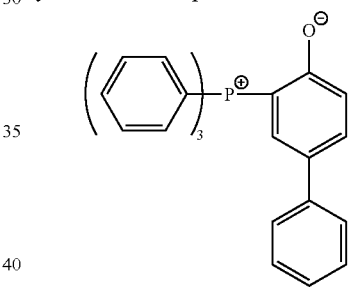

(Synthesis of Compound C7)

A compound was synthesized in the same manner as the compound C1 except that 13.0 g (0.076 mol) of tributylphosphine was used instead of triphenylphosphine, to thereby ultimately obtain 6.7 g of white crystal.

The thus obtained crystal was defined as a compound C7. As a result of analyses of the compound C7 by $^1$H-NMR, mass spectrometry, and elementary analysis, it was confirmed that the compound C7 was a target trisubstituted phosphoniophenolate represented by the following formula (20). The yield of the compound C7 was 30%.

(20)

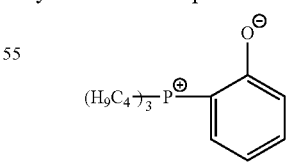

(Synthesis of Compound C8)

A compound was synthesized in the same manner as the compound C7 except that 12.3 g (0.100 mol) of m-methoxyaniline was used instead of o-methoxyaniline, to thereby ultimately obtain 6.0 g of white crystal.

The thus obtained crystal was defined as a compound C8. As a result of analyses of the compound C8 by $^1$H-NMR, mass spectrometry, and elementary analysis, it was confirmed that the compound C8 was a target trisubstituted phosphoniophenolate represented by the following formula (21). The yield of the compound C8 was 27%.

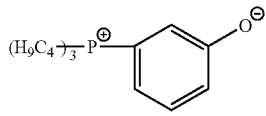
(21)

(Synthesis of Compound C9)

A compound was synthesized in the same manner as the compound C7 except that 12.3 g (0.100 mol) of p-methoxyaniline was used instead of o-methoxyaniline, to thereby ultimately obtain 7.8 g of white crystal.

The thus obtained crystal was defined as a compound C9. As a result of analyses of the compound C9 by $^1$H-NMR, mass spectrometry, and elementary analysis, it was confirmed that the compound C9 was a target trisubstituted phosphoniophenolate represented by the following formula (22). The yield of the compound C9 was 35%.

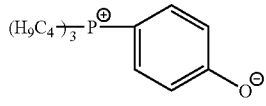
(22)

(Synthesis of Compound C10)

26.2 g (0.100 mol) of triphenylphosphine was dissolved in 75 ml of acetone in a 500 ml beaker at room temperature.

Then, 10.8 g (0.100 mol) of p-benzoquinone dissolved in 45 ml of acetone was slowly dropped into the solution in the beaker under stirring. As its dropping was continued, a precipitate was gradually produced.

After its dropping was completed, the solution in the beaker was being stirred for about 1 hour, and then was allowed to stand for about 30 minutes. Thereafter, a precipitated crystal was filtered and then dried to obtain 27.75 g of a greenish brown powder.

The thus obtained powder was defined as a compound C10. As a result of analyses of the compound C10 by $^1$H-NMR, mass spectrometry, and elementary analysis, it was confirmed that the compound C10 was a target adduct of triphenylphosphine with p-benzoquinone represented by the following formula (13). The yield of the compound C10 was 75%.

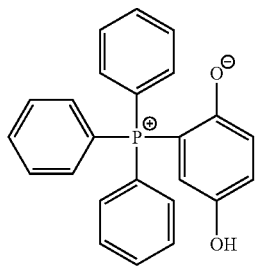
(13)

1-2 Preparation of Epoxy Resin Composition and Manufacture of Semiconductor Device Epoxy resin compositions of Examples and Comparative Examples were prepared using the obtained compounds C1 to C10 and triphenylphosphine, and further semiconductor devices of Examples and Comparative Examples were manufactured, as follows.

Example 1

First, biphenyl type epoxy resin represented by the formula (23) as the compound (A), phenol aralkyl resin represented by the formula (24) (wherein the number of repeat units is 3 and it is an average value) as the compound (B), the compound C1 as the curing accelerator (C), spherical fused silica (having an average particle size of 15 μm) as the inorganic filler (D), and carbon black, brominated bisphenol A type epoxy resin and carnauba wax as additives were prepared.

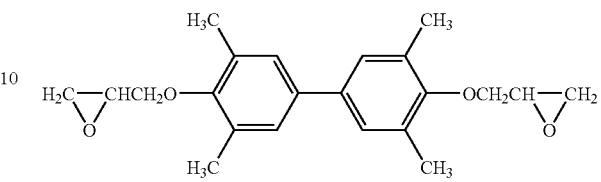
(23)

<Physical Properties of Compound Represented by the Formula (23)>

Melting point: 105° C.

Epoxy equivalent: 193

ICI melt viscosity at 150° C.: 0.15 poise

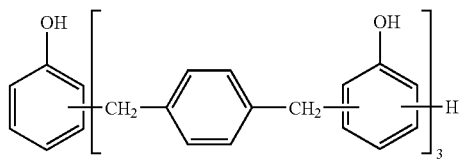
(24)

<Physical Properties of Compound Represented by the Formula (24)>

Softening point: 77° C.

Hydroxyl equivalent: 172

ICI melt viscosity at 150° C.: 3.6 poise

Then, 52 parts by weight of biphenyl type epoxy resin, 48 parts by weight of phenol aralkyl resin, 1.77 parts by weight of the compound C1, 730 parts by weight of spherical fused silica, 2 parts by weight of carbon black, 2 parts by weight of brominated bisphenol A type epoxy resin, and 2 parts by weight of carnauba wax were mixed at room temperature. Thereafter, the mixture was kneaded using a hot roll at 95° C. for 8 minutes, and was cooled and then ground, to thereby obtain an epoxy resin composition (thermosetting resin composition).

Next, 8 packages of 100-pin TQFP (semiconductor devices) and 15 packages of 16-pin DIP (semiconductor devices) were manufactured using the obtained epoxy resin composition as a mold resin.

The 100-pin TQFP packages were manufactured by subjecting the epoxy resin composition to transfer molding under the conditions of a mold temperature of 175° C., an injection pressure of 7.4 MPa and a curing time of 2 minutes, and then after-curing the molded product at 175° C. for 8 hours.

In this regard, it is to be noted that this 100-pin TQFP package has a size of 14×14 mm and a thickness of 1.4 mm, a silicon chip (semiconductor element) has a size of 8.0×8.0 mm, and a lead frame is made of alloy 42.

The 16-pin DIP packages were manufactured by subjecting the epoxy resin composition to transfer molding under the conditions of a mold temperature of 175° C., an injection pressure of 6.8 MPa and a curing time of 2 minutes, and then after-curing the molded product at 175° C. for 8 hours.

In this regard, it is to be noted that this 16-pin DIP package has a size of 6.4×19.8 mm and a thickness of 3.5 mm, a silicon chip (semiconductor element) has a size of 3.5×3.5 mm, and a lead frame is made of alloy 42.

Example 2

First, biphenyl aralkyl type epoxy resin represented by the formula (25) (wherein the number of repeat units is 3 and it is an average value) as the compound (A), biphenyl aralkyl type phenolic resin represented by the formula (26) (wherein the number of repeat units is 3 and it is an average value) as the compound (B), the compound C1 as the curing accelerator (C), spherical fused silica (having an average particle size of 15 μm) as the inorganic filler (D), and carbon black, brominated bisphenol A type epoxy resin and carnauba wax as additives were prepared.

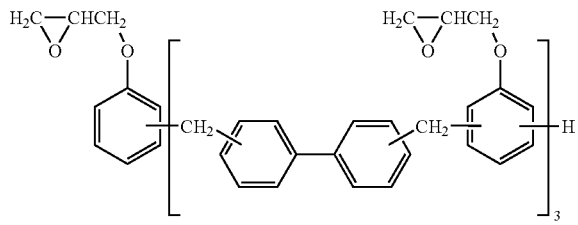

(25)

<Physical Properties of Compound Represented by the Formula (25)>

Softening point: 60° C.

Epoxy equivalent: 272

ICI melt viscosity at 150° C.: 1.3 poise

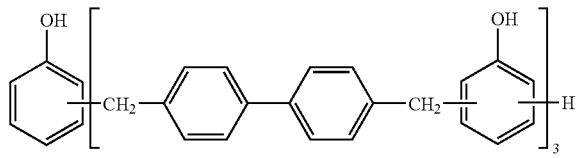

(26)

<Physical Properties of Compound Represented by the Formula (26)>

Softening point: 68° C.

Hydroxyl equivalent: 199

ICI melt viscosity at 150° C.: 0.9 poise

Then, 57 parts by weight of biphenyl aralkyl type epoxy resin, 43 parts by weight of biphenyl aralkyl type phenolic resin, 1.77 parts by weight of the compound C1, 650 parts by weight of spherical fused silica, 2 parts by weight of carbon black, 2 parts by weight of brominated bisphenol A type epoxy resin, and 2 parts by weight of carnauba wax were mixed at room temperature. Thereafter, the mixture was kneaded using a hot roll at 105° C. for 8 minutes, and was cooled and then ground, to thereby obtain an epoxy resin composition (thermosetting resin composition).

Then, packages (semiconductor devices) were manufactured in the same manner as Example 1 except that the epoxy resin composition prepared in Example 2 was used as a mold resin.

Example 3

An epoxy resin composition (thermosetting resin composition) of Example 3 was prepared in the same manner as Example 1 except that the compound C2 was used instead of the compound C1, and packages (semiconductor devices) of Example 3 were manufactured in the same manner as Example 1 except that the epoxy resin composition prepared in Example 3 was used as a mold resin.

Example 4

An epoxy resin composition (thermosetting resin composition) of Example 4 was prepared in the same manner as Example 2 except that the compound C2 was used instead of the compound C1, and packages (semiconductor devices) of Example 4 were manufactured in the same manner as Example 2 except that the epoxy resin composition prepared in Example 4 was used as a mold resin.

Example 5

An epoxy resin composition (thermosetting resin composition) of Example 5 was prepared in the same manner as Example 1 except that the compound C3 was used instead of the compound C1, and packages (semiconductor devices) of Example 5 were manufactured in the same manner as Example 1 except that the epoxy resin composition prepared in Example 5 was used as a mold resin.

Example 6

An epoxy resin composition (thermosetting resin composition) of Example 6 was prepared in the same manner as Example 2 except that the compound C3 was used instead of the compound C1, and packages (semiconductor devices) of Example 6 were manufactured in the same manner as Example 2 except that the epoxy resin composition prepared in Example 6 was used as a mold resin.

Example 7

An epoxy resin composition (thermosetting resin composition) of Example 7 was prepared in the same manner as Example 1 except that 2.05 parts by weight of the compound C4 was used instead of the compound C1, and packages (semiconductor devices) of Example 7 were manufactured in the same manner as Example 1 except that the epoxy resin composition prepared in Example 7 was used as a mold resin.

Example 8

An epoxy resin composition (thermosetting resin composition) of Example 8 was prepared in the same manner as Example 2 except that 2.05 parts by weight of the compound C4 was used instead of the compound C1, and packages (semiconductor devices) of Example 8 were manufactured in the same manner as Example 2 except that the epoxy resin composition prepared in Example 8 was used as a mold resin.

Example 9

An epoxy resin composition (thermosetting resin composition) of Example 9 was prepared in the same manner as Example 1 except that 2.01 parts by weight of the compound C5 was used instead of the compound C1, and packages (semiconductor devices) of Example 9 were manufactured in the same manner as Example 1 except that the epoxy resin composition prepared in Example 9 was used as a mold resin.

Example 10

An epoxy resin composition (thermosetting resin composition) of Example 10 was prepared in the same manner as Example 2 except that 2.01 parts by weight of the compound C5 was used instead of the compound C1, and packages (semiconductor devices) of Example 10 were manufactured in the same manner as Example 2 except that the epoxy resin composition prepared in Example 10 was used as a mold resin.

Example 11

An epoxy resin composition (thermosetting resin composition) of Example 11 was prepared in the same manner as Example 1 except that 2.15 parts by weight of the compound C6 was used instead of the compound C1, and packages (semiconductor devices) of Example 11 were manufactured in the same manner as Example 1 except that the epoxy resin composition prepared in Example 11 was used as a mold resin.

Example 12

An epoxy resin composition (thermosetting resin composition) of Example 12 was prepared in the same manner as Example 2 except that 2.15 parts by weight of the compound C6 was used instead of the compound C1, and packages (semiconductor devices) of Example 12 were manufactured in the same manner as Example 2 except that the epoxy resin composition prepared in Example 12 was used as a mold resin.

Example 13

An epoxy resin composition (thermosetting resin composition) of Example 13 was prepared in the same manner as Example 1 except that 1.47 parts by weight of the compound C7 was used instead of the compound C1, and packages (semiconductor devices) of Example 13 were manufactured in the same manner as Example 1 except that the epoxy resin composition prepared in Example 13 was used as a mold resin.

Example 14

An epoxy resin composition (thermosetting resin composition) of Example 14 was prepared in the same manner as Example 2 except that 1.47 parts by weight of the compound C7 was used instead of the compound C1, and packages (semiconductor devices) of Example 14 were manufactured in the same manner as Example 2 except that the epoxy resin composition prepared in Example 14 was used as a mold resin.

Example 15

An epoxy resin composition (thermosetting resin composition) of Example 15 was prepared in the same manner as Example 13 except that the compound C8 was used instead of the compound C7, and packages (semiconductor devices) of Example 15 were manufactured in the same manner as Example 1 except that the epoxy resin composition prepared in Example 15 was used as a mold resin.

Example 16

An epoxy resin composition (thermosetting resin composition) of Example 16 was prepared in the same manner as Example 14 except that the compound C8 was used instead of the compound C7, and packages (semiconductor devices) of Example 16 were manufactured in the same manner as Example 2 except that the epoxy resin composition prepared in Example 16 was used as a mold resin.

Example 17

An epoxy resin composition (thermosetting resin composition) of Example 17 was prepared in the same manner as Example 13 except that the compound C9 was used instead of the compound C7, and packages (semiconductor devices) of Example 17 were manufactured in the same manner as Example 1 except that the epoxy resin composition prepared in Example 17 was used as a mold resin.

Example 18

An epoxy resin composition (thermosetting resin composition) of Example 18 was prepared in the same manner as Example 14 except that the compound C9 was used instead of the compound C7, and packages (semiconductor devices) of Example 18 were manufactured in the same manner as Example 2 except that the epoxy resin composition prepared in Example 18 was used as a mold resin.

Comparative Example 1

An epoxy resin composition (thermosetting resin composition) of Comparative Example 1 was prepared in the same manner as Example 1 except that 1.85 parts by weight of the compound C10 was used instead of the compound C1, and packages (semiconductor devices) of Comparative Example 1 were manufactured in the same manner as Example 1 except that the epoxy resin composition prepared in Comparative Example 1 was used as a mold resin.

Comparative Example 2

An epoxy resin composition (thermosetting resin composition) of Comparative Example 2 was prepared in the same manner as Example 2 except that 1.85 parts by weight of the compound C10 was used instead of the compound C1, and packages (semiconductor devices) of Comparative Example 2 were manufactured in the same manner as Example 2 except that the epoxy resin composition prepared in Comparative Example 2 was used as a mold resin.

Comparative Example 3

An epoxy resin composition (thermosetting resin composition) of Comparative Example 3 was prepared in the same manner as Example 1 except that 1.00 part by weight of triphenylphosphine was used instead of the compound C1, and packages (semiconductor packages) of Comparative Example 3 were manufactured in the same manner as Example 1 except that the epoxy resin composition prepared in Comparative Example 3 was used as a mold resin.

Comparative Example 4

An epoxy resin composition (thermosetting resin composition) of Comparative Example 4 was prepared in the same manner as Example 2 except that 1.00 part by weight of triphenylphosphine was used instead of the compound C1, and packages (semiconductor devices) of Comparative Example 4 were manufactured in the same manner as Example 2 except that the epoxy resin composition prepared in Comparative Example 4 was used as a mold resin.

1-3 Characteristic Evaluation

For each of the epoxy resin compositions obtained in Examples and Comparative Examples, characteristic evaluations (I) to (III) were made as follows. Further, for each of the semiconductor devices obtained in Examples and Comparative Examples, characteristic evaluations (IV) and (V) were made as follows.

(I) Spiral Flow

The spiral flow of each of the epoxy resin compositions was measured using a mold for spiral flow test according to EMMI-I-66, under the conditions of a mold temperature of 175° C., an injection pressure of 6.8 MPa, and a curing time of 2 minutes.

The spiral flow is a parameter of fluidity. Here, larger spiral flow means better fluidity.

(II) Curing Torque

The torque after 45 seconds at 175° C. of each of the epoxy resin compositions was measured using a curelastometer ("JSR curelastometer IV PS model" manufactured by Orientech Co., Ltd.). Here, larger curing torque means better curability.

(III) Residual Flow Percentage

Each of the epoxy resin compositions was preserved at 30° C. for 1 week in atmospheric air, and thereafter the spiral flow thereof was measured in the same manner as described above. Then, the percentage (%) of the thus obtained spiral flow was determined on the basis of the initial spiral flow of the epoxy resin composition just after the preparation. Here, larger residual flow percentage means better storage stability.

(IV) Solder Cracking Resistance

Each of the 100-pin TQFP packages was left at 85° C. and at 85% relative humidity for 168 hours, and was then immersed in a solder bath at 260° C. for 10 seconds.

Thereafter, each package was observed under a microscope to determine whether or not cracking occurred in its surface.

The occurrence rate of cracking was obtained as a percentage (%) by calculating using the following formula.

Occurrence rate of cracking=(the number of packages in which cracking occurred/the total number of manufactured packages)×100

Here, smaller occurrence rate of cracking means better solder cracking resistance.

Further, an area where delamination occurred between the silicon chip and the cured product of the epoxy resin composition was measured using a reflectoscope. Then, the delamination ratio of the semiconductor package was obtained as a percentage (%) by calculating using the following formula. Practically, an average value of 8 semiconductor packages was used for evaluation.

Delamination ratio=(area where delamination occurred)/(area of silicon chip)×100

Here, smaller delamination ratio means better solder cracking resistance.

(V) Moisture Resistance Reliability

A voltage of 20 V was applied to each of the 16-pin DIP packages in water vapor at 125° C. and at 100% relative humidity, and each package was then checked whether or not conduction failure occurred therein. The time until the conduction failure occurred in 8 or more packages of the 15 packages was measured and the time was defined as a failure time.

In this regard, it is to be noted that the measuring time was 500 hours at longest, and in a case where the number of failed packages at that time was less than 8, the failure time was shown as "more than 500 hours (>500)". Here, longer failure time means better moisture resistance reliability.

The results of the characteristic evaluations (I) to (V) are shown in Table 1.

TABLE 1

| | | Epoxy Resin Composition | | | Package | | |
|---|---|---|---|---|---|---|---|
| | | | | | Solder Cracking Resistance | Solder Cracking Resistance | Moisture Resistance Reliability |
| | Curing Accelerator | Spiral Flow (cm) | Curing Torque (N·m) | Residual Flow Percentage (%) | (Occurrence Rate of Cracking: %) | (Delamination Ratio: %) | (Failure Time: hr) |
| Example 1 | Compound C1 | 114 | 7.25 | 91 | 0 | 0 | >500 |
| Example 2 | | 108 | 7.86 | 93 | 0 | 0 | >500 |
| Example 3 | Compound C2 | 120 | 6.92 | 90 | 0 | 0 | >500 |
| Example 4 | | 117 | 7.16 | 94 | 0 | 0 | >500 |
| Example 5 | Compound C3 | 108 | 7.41 | 92 | 5 | 0 | >500 |
| Example 6 | | 104 | 8.01 | 95 | 5 | 0 | >500 |
| Example 7 | Compound C4 | 107 | 7.76 | 94 | 0 | 0 | >500 |
| Example 8 | | 102 | 8.22 | 95 | 0 | 0 | >500 |
| Example 9 | Compound C5 | 110 | 7.38 | 85 | 0 | 0 | >500 |
| Example 10 | | 100 | 7.55 | 88 | 0 | 0 | >500 |
| Example 11 | Compound C6 | 106 | 7.96 | 95 | 0 | 0 | >500 |
| Example 12 | | 102 | 8.11 | 98 | 0 | 0 | >500 |
| Example 13 | Compound C7 | 109 | 7.49 | 90 | 0 | 0 | >500 |
| Example 14 | | 103 | 8.02 | 92 | 0 | 0 | >500 |
| Example 15 | Compound C8 | 114 | 7.03 | 90 | 0 | 0 | >500 |
| Example 16 | | 111 | 7.24 | 93 | 0 | 0 | >500 |
| Example 17 | Compound C9 | 103 | 7.60 | 92 | 0 | 5 | >500 |
| Example 18 | | 99 | 8.39 | 89 | 0 | 5 | >500 |
| Com. Example 1 | Compound C10 | 105 | 7.00 | 55 | 20 | 15 | 480 |
| Com. Example 2 | | 99 | 7.15 | 47 | 20 | 15 | 480 |
| Com. Example 3 | Triphenylphosphine | 77 | 3.90 | 43 | 20 | 5 | >500 |
| Com. Example 4 | | 65 | 4.33 | 51 | 20 | 5 | >500 |

As shown in Table 1, each of the epoxy resin compositions obtained in Examples 1 to 18 (epoxy resin compositions of the present invention) had extremely excellent curability, storage stability and fluidity. Further, each of the packages of Examples 1 to 18 (semiconductor devices of the present invention) encapsulated with a cured product of each of the epoxy resin compositions of Examples 1 to 18, respectively had excellent solder cracking resistance and moisture resistance reliability.

Further, the semiconductor devices manufactured in Examples 1 to 4, in which the compound C1 or the compound C2 was used as a curing accelerator had improved solder cracking resistance as compared with the semiconductor devices manufactured in Examples 5 and 6, in which the compound C3 was used as a curing accelerator. Also, the semiconductor devices manufactured in Examples 13 to 16, in which the compound C7 or the compound C8 was used as a curing accelerator had improved solder cracking resistance as compared with the semiconductor devices manufactured in Examples 17 and 18, in which the compound C9 was used as a curing accelerator. From these results, it is confirmed that by using trisubstituted phosphoniophenolate in which the oxyanion is located in ortho position or meta position to the phosphorus atom, as a curing accelerator, an obtained semiconductor package can have improved solder cracking resistance as compared with the case where trisubstituted phosphoniophenolate in which the oxyanion is located in para position to the phosphorus atom is used.

On the other hand, each of the epoxy resin compositions obtained in Comparative Examples 1 and 2 had poor storage stability, and each of the packages obtained in Comparative Examples 1 and 2 had poor solder cracking resistance and extremely low moisture resistance reliability. Further, each of the epoxy resin compositions obtained in Comparative Examples 3 and 4 had extremely poor curability, storage stability and fluidity, and each of the packages obtained in Comparative Examples 3 and 4 had poor solder cracking resistance.

Examples 19 to 27, Comparative Examples 5 and 6

Epoxy resin compositions (thermosetting resin compositions) of Examples 19 to 27 and Comparative Examples 5 and 6 were prepared in the same manner as Examples 1, 3, 5, 7, 9, 11, 13, 15 and 17 and Comparative Examples 1 and 3, respectively, except that a mixture of 26 parts by weight of biphenyl type epoxy resin represented by the formula (23) and 28.5 parts by weight of biphenyl aralkyl type epoxy resin represented by the formula (25) as the compound (A), and 45.5 parts by weight of phenol aralkyl resin represented by the formula (24) as the compound (B) were used. Further, packages (semiconductor devices) of Examples 19 to 27 and Comparative Examples 5 and 6 were manufactured in the same manner as Example 1 except that the epoxy resin compositions prepared in Examples 19 to 27 and Comparative Examples 5 and 6 were used, respectively.

For each of the epoxy resin compositions and each of the packages obtained in Examples 19 to 27 and Comparative Examples 5 and 6, characteristic evaluations were made in the same manner described above. Their measurement results were substantially the same as those of Examples 1, 3, 5, 7, 9, 11, 13, 15 and 17 and Comparative Examples 1 and 3 shown in Table 1, respectively.

Examples 28 to 36 and Comparative Examples 7 and 8

Epoxy resin compositions (thermosetting resin compositions) of Examples 28 to 36 and Comparative Examples 7 and 8 were prepared in the same manner as Examples 1, 3, 5, 7, 9, 11, 13, 15 and 17 and Comparative Examples 1 and 3, respectively, except that 54.5 parts by weight of biphenyl type epoxy resin represented by the formula (23) as the compound (A), and a mixture of 24 parts by weight of phenol aralkyl resin represented by the formula (24) and 21.5 parts by weight of biphenyl aralkyl type phenolic resin represented by the formula (26) as the compound (B) were used. Further, packages (semiconductor devices) of Examples 28 to 36 and Comparative Examples 7 and 8 were manufactured in the same manner as Example 1 except that the epoxy resin compositions prepared in Examples 28 to 36 and comparative Examples 7 and 8 were used, respectively.

For each of the epoxy resin compositions and each of the packages obtained in Examples 28 to 36 and Comparative Examples 7 and 8, characteristic evaluations were made in the same manner described above. Their measurement results were substantially the same as those of Examples 1, 3, 5, 7, 9, 11, 13, 15 and 17 and Comparative Examples 1 and 3 shown in Table 1, respectively.

Examples 37 to 45 and comparative Example 9

Resin compositions (thermosetting resin compositions) of Examples 37 to 45 and Comparative Example 9 were prepared by blending 100 parts by weight of bismaleimide resin composed of diaminodiphenylmethane (BMI-H made by K-I CHEMICAL, INDUSTRY Co., LTD.) with each of the compounds C1 to C9 and triphenylphosphine as a curing accelerator at the blending ratio shown in Table 2, respectively, and homogeneously mixing them.

For each of the resin compositions obtained in Examples 37 to 45 and Comparative Example 9, gel time at 175° C. was measured. The measurement results and the blending ratio of each of the curing accelerators are shown in Table 2.

TABLE 2

| | Curing Accelerator | | |
|---|---|---|---|
| | Kind | Blending Ratio (parts by weight) | Gel Time (second) |
| Example 37 | Compound C1 | 1.77 | 38 |
| Example 38 | Compound C2 | 1.77 | 40 |
| Example 39 | Compound C3 | 1.77 | 36 |
| Example 40 | Compound C4 | 2.05 | 36 |
| Example 41 | Compound C5 | 2.01 | 31 |
| Example 42 | Compound C6 | 2.15 | 37 |
| Example 43 | Compound C7 | 1.47 | 37 |
| Example 44 | Compound C8 | 1.47 | 40 |
| Example 45 | Compound C9 | 1.47 | 35 |
| Com. Example 9 | Triphenylphosphine | 1.00 | Microgel |

As shown in Table 2, each of the resin compositions obtained in Examples 37 to 45 was immediately cured. On the other hand, the resin composition obtained in comparative Example 9 was not cured but micro-gelled.

2 Evaluation of Trisubstituted Phosphoniophenolate Salts

First, compounds C11 to C20 were prepared as a curing accelerator.

2-1 Synthesis of Curing Accelerator

Each of the compounds C11 to C20 was synthesized as follows.

(Synthesis of Compound C11)

12.3 g of o-methoxyaniline (0.100 mol) and an aqueous hydrochloric acid solution which had been prepared by dissolving 25 ml of concentrated hydrochloric acid (37%) in 200 ml of pure water in advance were put into a 500 ml separable flask equipped with a condenser and a stirrer, and they were stirred to dissolve o-methoxyaniline.

Thereafter, the separable flask was cooled with ice such that the temperature in the flask was held at 0 to 5° C., and in this state 7.2 g (0.104 mol) of sodium nitrite dissolved in 20 ml of pure water was slowly dropped into the solution in the flask.

Then, 20.0 g (0.076 mol) of triphenylphosphine dissolved in 150 ml of ethyl acetate was dropped into the separable flask and then the solution in the flask was stirred for 20 minutes.

Then, 8.0 g (0.200 mol) of sodium hydroxide dissolved in 20 ml of pure water was slowly dropped into the separable flask, and then the solution in the flask was strongly stirred for about 1 hour.

After bubbling of nitrogen gas was very slight, dilute hydrochloric acid was added until pH reached 3.0 or below, and 30 g (0.200 mol) of sodium iodide was then added. Then, a resultant precipitate was filtered and then dried to obtain 29.7 g of reddish brown crystal of 2-methoxyphenyl triphenylphosphonium iodide.

Next, 29.7 g (0.060 mol) of the obtained 2-methoxyphenyl triphenylphosphonium iodide, 88.7 g (0.769 mol) of pyridine hydrochloride, and 12.0 g (0.118 mol) of acetic anhydride were put into a 500 ml separable flask equipped with a condenser and a stirrer, and they were heated at 200° C. for 5 hours under reflux and stirring.

After reaction was completed, the reaction product was cooled to room temperature, and then 3.3 g (0.022 mol) of sodium iodide dissolved in 250 ml of pure water was put into the flask. Then, a precipitated solid was filtered and then dried to obtain 24.1 g of a brown solid of 2-hydroxyphenyl triphenylphosphonium iodide.

Next, 24.1 g (0.050 mol) of the thus obtained 2-hydroxyphenyl triphenylphosphonium iodide, 12.5 g (0.050 mol) of bisphenol S (2,2-bis(4-hydroxyphenyl)sulfone), and 180 ml of methanol were put into a 500 ml beaker, and they were stirred.

Then, 2 g (0.050 mol) of sodium hydroxide dissolved in 200 ml of methanol was dropped into the beaker, and then the solution in the beaker was stirred for 30 minutes.

Then, the reaction product was dropped into 2,000 ml of pure water. Then, a precipitated solid was filtered and then dried to obtain 10.2 g of a brown solid which is a salt of 2-hydroxyphenyl triphenylphosphonium with bisphenol S.

The thus obtained solid was defined as a compound C11. As a result of analyses of the compound C11 by $^1$H-NMR, mass spectrometry and elementary analysis, it was confirmed that the compound C11 was a target trisubstituted phosphoniophenolate salt represented by the following formula (27). The yield of the compound C11 was 22%.

(27)

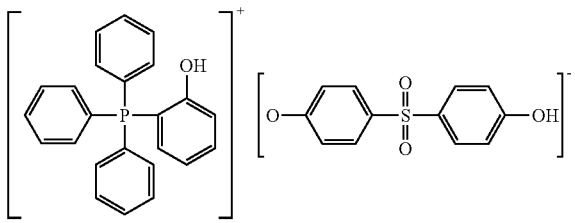

(Synthesis of Compound C12)

A compound was synthesized in the same manner as the compound C11 except that 8.0 g (0.050 mol) of 2,3-dihydroxynaphthalene was used instead of bisphenol S (2,2-bis(4-hydroxyphenyl)sulfone), to thereby ultimately obtain 10.8 g of brown crystal.

The thus obtained crystal was defined as a compound C12. As a result of analyses of the compound C12 by $^1$H-NMR, mass spectrometry and elementary analysis, it was confirmed that the compound C12 was a target trisubstituted phosphoniophenolate salt represented by the following formula (28). The yield of the compound C12 was 42%.

(28)

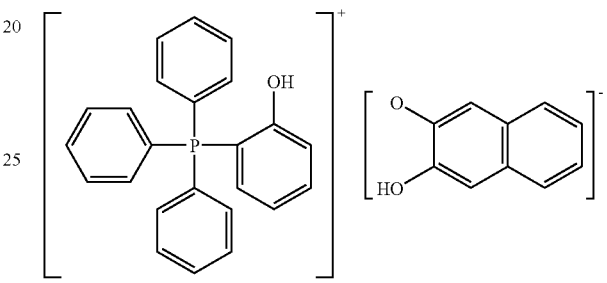

(Synthesis of Compound C13)

A compound was synthesized in the same manner as the compound C11 except that 12.3 g (0.100 mol) of m-methoxyaniline was used instead of o-methoxyaniline, 16.0 g (0.100 mol) of 2,3-dihydroxynaphthalene was used instead of 12.5 g of bisphenol S (2,2-bis(4-hydroxyphenyl)sulfone), and that an addition amount of sodium hydroxide was changed to 4.0 g (0.100 mol), to thereby ultimately obtain 17.5 g of pink crystal.

The thus obtained crystal was defined as a compound C13. As a result of analyses of the compound C13 by $^1$H-NMR, mass spectrometry and elementary analysis, it was confirmed that the compound C13 was a target trisubstituted phosphoniophenolate salt represented by the following formula (29). The yield of the compound C13 was 52%.

(29)

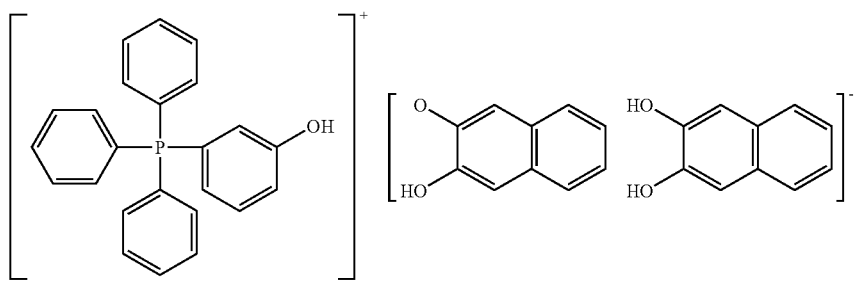

(Synthesis of Compound C14)

A compound was synthesized in the same manner as compound C13 except that 12.3 g (0.100 mol) of p-methoxyaniline was used instead of m-methoxyaniline, to thereby ultimately obtain 18.1 g of white crystal.

The thus obtained crystal was defined as a compound C14. As a result of analyses of the compound C14 by ¹H-NMR, mass spectrometry and elementary analysis, it was confirmed that the compound C14 was a target trisubstituted phosphoniophenolate salt represented by the following formula (30). The yield of the compound C14 was 54%.

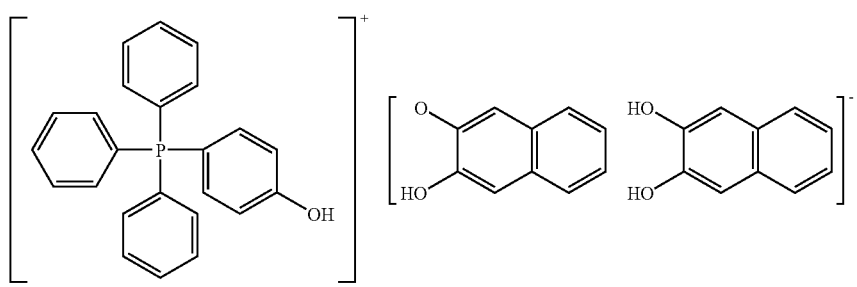

(30)

(Synthesis of Compound C15)

A compound was synthesized in the same manner as compound C11 except that 13.7 g (0.100 mol) of 2-methoxy-5-methylaniline was used instead of o-methoxyaniline, 23.1 g (0.076 mol) of tri-p-tolylphosphine was used instead of triphenylphosphine, and that 8.0 g (0.050 mol) of 1,6-dihydroxynaphthalene was used instead of 12.5 g of bisphenol S (2,2-bis(4-hydroxyphenyl)sulfone), to thereby ultimately obtain 14.6 g of pale yellowish white crystal.

The thus obtained crystal was defined as a compound C15. As a result of analyses of the compound C15 by ¹H-NMR, mass spectrometry and elementary analysis, it was confirmed that the compound C15 was a target trisubstituted phosphoniophenolate salt represented by the following formula (31). The yield of the compound C15 was 51%.

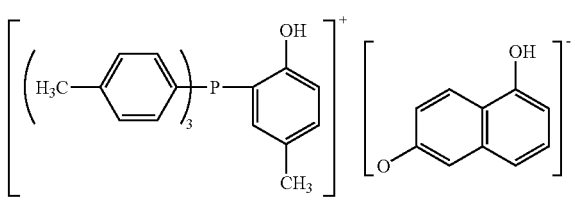

(31)

(Synthesis of Compound C16)

A compound was synthesized in the same manner as the compound C11 except that 13.7 g (0.100 mol) of 2-methoxy-5-methylaniline was used instead of o-methoxyaniline, and that 23.1 g (0.076 mol) of tri-p-tolylphosphine was used instead of triphenylphsophine, to thereby ultimately obtain 16.8 g of yellow crystal.

The thus obtained crystal was defined as a compound C16. As a result of analyses of the compound C16 by ¹H-NMR, mass spectrometry and elementary analysis, it was confirmed that the compound C16 was a target trisubstituted phosphoniophenolate salt represented by the following formula (32). The yield of the compound C16 was 51%.

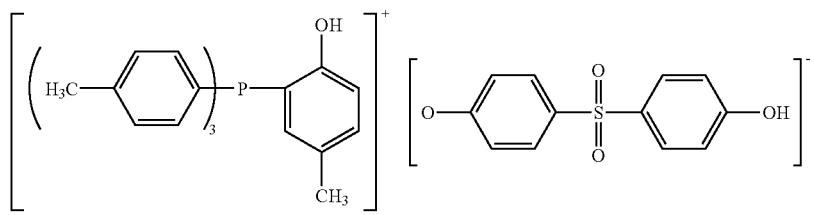

(32)

(Synthesis of Compound C17)

A compound was synthesized in the same manner as the compound C11 except that 26.8 g (0.076 mol) of tris (4-methoxyphenyl)phosphine was used instead of triphenylphosphine, and that 20.0 g (0.100 mol) of bis(4-hydroxyphenyl) methane was used instead of bisphenol S (2,2-bis(4-hydroxyphenyl)sulfone), to thereby ultimately obtain 5.4 g of white crystal.

The thus obtained crystal was defined as a compound C17. As a result of analyses of the compound C17 by ¹H-NMR, mass spectrometry and elementary analysis, it was confirmed that the compound C17 was a target trisubstituted phosphoniophenolate salt represented by the following formula (33). The yield of the compound C17 was 18%.

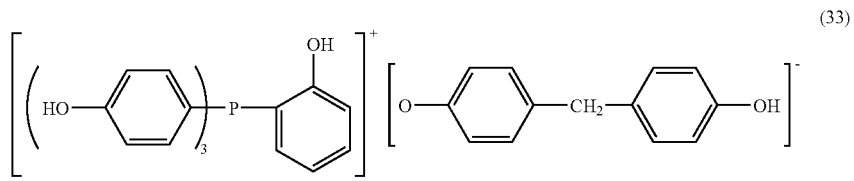

(Synthesis of Compound C18)

40.0 g (0.2 mol) of bisphenol F-D (a mixture of the isomers of bisphenol F, which is made by HONSHU Chemical INDUSTRY CO., LTD.) and 50 ml of methanol were put into a 1-liter separable flask equipped with a stirrer, and they were stirred at room temperature to dissolve bisphenol F-D. Further, a solution which had been prepared by dissolving 4.0 g (0.1 mol) of sodium hydroxide in 50 ml of methanol in advance was added to the solution in the flask under stirring. Then, a solution which had been prepared by dissolving 41.9 g (0.1 mol) of tetraphenylphosphonium bromide in 150 ml of methanol in advance was added. The solution in the flask was being stirred for a while, and 300 ml of methanol was then added. Thereafter, the solution in the flask was dropped into a large amount of water under stirring, to thereby obtain a white precipitate.

The thus obtained precipitate was defined as a compound C18. As a result of analyses of the compound C18 by $^1$H-NMR, mass spectrometry and elementary analysis, it was confirmed that the compound C18 was a target trisubstituted phosphoniophenolate salt represented by the following formula (34). The yield of the compound C18 was 57%.

Next, 27.75 g (0.075 mol) of the obtained greenish brown powder, 3.5 g (0.075 mol) of formic acid, and 180 ml of methanol were put into a 500 ml beaker, and they were stirred.

Then, 3 g (0.075 mol) of sodium hydroxide dissolved in 200 ml of methanol was dropped into the beaker, and then the solution in the beaker was stirred for 30 minutes.

Then, the reaction product was dropped into 2,000 ml of pure water. A precipitated solid was filtered and then dried, to thereby obtain 13.4 g of a brown solid.

The thus obtained solid was defined as a compound C19. As a result of analyses of the compound C19 by $^1$H-NMR, mass spectrometry and elementary analysis, it was confirmed that the compound C19 was a target trisubstituted phosphoniophenolate salt represented by the following formula (35). The yield of the compound C19 was 25%.

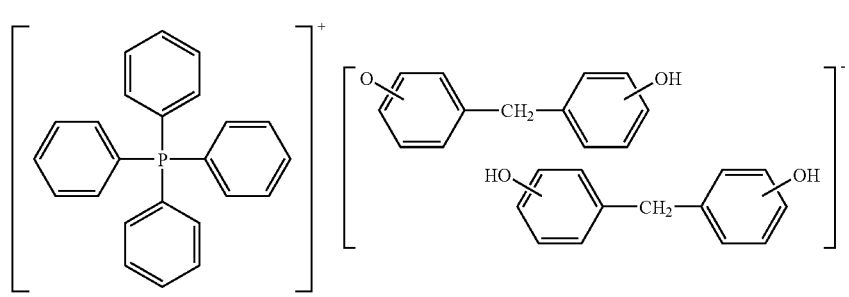

(Synthesis of Compound C19)

In a 500 ml beaker, 26.2 g (0.100 mol) of triphenylphosphine was dissolved in 75 ml of acetone at room temperature.

Then, 10.8 g (0.100 mol) of p-benzoquinone dissolved in 45 ml of acetone, was slowly dropped into the solution in the beaker under stirring. As its dropping was continued, a precipitate was gradually produced.

After its dropping was completed, a resultant solution was stirred for about 1 hour and then was allowed to stand for about 30 minutes.

Thereafter, a precipitated crystal was filtered and then dried, to thereby obtain 27.75 g of a greenish brown powder.

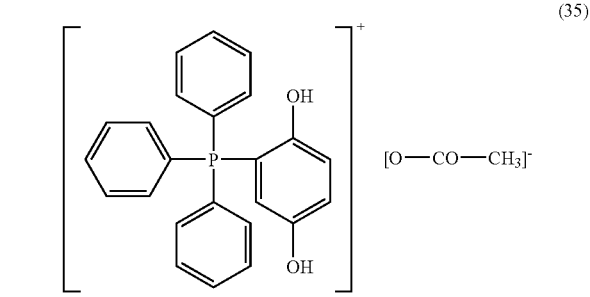

(Synthesis of Compound C20)

A compound was synthesized in the same manner as the compound C19 except that 18.8 g (0.075 mol) of bisphenol S (2,2-bis(4-hydroxyphenyl)sulfone) was used instead of formic acid, to thereby ultimately obtain 30.2 g of brown crystal.

The thus obtained crystal was defined as a compound C20. As a result of analyses of the compound C20 by $^1$H-NMR, mass spectrometry and elementary analysis, it was confirmed that the compound C20 was a target trisubstituted phosphoniophenolate salt represented by the following formula (36). The yield of the compound C20 was 49%.

(36)

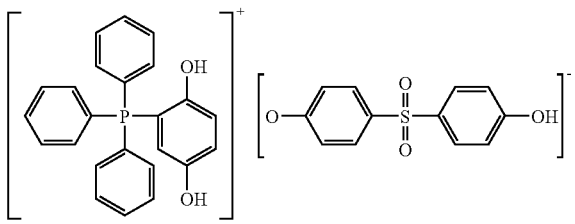

2-2 Preparation of Epoxy Resin Composition and Manufacture of Semiconductor Device Epoxy resin compositions of Examples 46 to 59 and Comparative Examples 10 to 15 were prepared using the obtained compounds C11 to C20, respectively, and semiconductor packages of Examples 46 to 59 and Comparative Examples 10 to 15 were manufactured, as follows.

Example 46

First, biphenyl type epoxy resin represented by the formula (23) as the compound (A), phenol aralkyl resin represented by the formula (24) (wherein the number of repeat units is 3 and it is an average number) as the compound (B), the compound C11 as the curing accelerator (C), spherical fused silica (having an average particle size of 15 μm) as the inorganic filler (D), and carbon black, brominated bisphenol A type epoxy resin and carnauba wax as additives were prepared.

Then, 52 parts by weight of biphenyl type epoxy resin, 48 parts by weight of phenol aralkyl resin, 3.02 parts by weight of the compound C11, 730 parts by weight of spherical fused silica, 2 parts by weight of carbon black, 2 parts by weight of brominated bisphenol A type epoxy resin and 2 parts by weight of carnauba wax were mixed at room temperature. Thereafter, the obtained mixture was kneaded using a hot roll at 95° C. for 8 minutes, and was cooled and then ground, to thereby obtain an epoxy resin composition (thermosetting resin composition).

Next, 8 packages of 100-pin TQFP (semiconductor devices) and 15 packages of 16-pin DIP (semiconductor devices) were manufactured using the obtained epoxy resin composition as a mold resin.

The 100-pin TQFP packages were manufactured by subjecting the epoxy resin composition to transfer molding, under the conditions of a mold temperature of 175° C., an injection pressure of 7.4 MPa, and a curing time of 2 minutes, and then after-curing the molded product at 175° C. for 8 hours.

In this regard, it is to be noted that this 100-pin TQFP package has a size of 14×14 mm and a thickness of 1.4 mm, a silicon chip (semiconductor element) has a size of 8.0×8.0 mm, and that a lead frame is made of alloy 42.

The 16-pin DIP packages were manufactured by subjecting the epoxy resin composition to transfer molding under the conditions of a mold temperature of 175° C., an injection pressure of 6.8 MPa, and a curing time of 2 minutes, and then after-curing the molded product at 175° C. for 8 hours.

In this regard, it is to be noted that this 16-pin DIP package has a size of 6.4×19.8 mm and a thickness of 3.5 mm, a silicon chip (semiconductor element) has a size of 3.5×3.5 mm, and a lead frame is made of alloy 42.

Example 47

First, biphenyl aralkyl type epoxy resin represented by the formula (25) (wherein the number of repeat units is 3 and it is an average number) as the compound (A), biphenyl aralkyl type phenolic resin represented by the formula (26) (wherein the number of repeat units is 3 and it is an average number) as the compound (B), the compound C11 as the curing accelerator (C), spherical fused silica (having an average particle size of 15 μm) as the inorganic filler (D), and carbon black, brominated bisphenol A type epoxy resin and carnauba wax as additives were prepared.

Then, 57 parts by weight of biphenyl aralkyl type epoxy resin, 43 parts by weight of biphenyl aralkyl type phenolic resin, 3.02 parts by weight of the compound C11, 650 parts by weight of spherical fused silica, 2 parts by weight of carbon black, 2 parts by weight of brominated bisphenol A type epoxy resin and 2 parts by weight of carnauba wax were mixed at room temperature. Thereafter, the obtained mixture was kneaded using a hot roll at 105° C. for 8 minutes, and was cooled and then ground, to thereby obtain an epoxy resin composition (thermosetting resin composition).

Next, packages (semiconductor devices) were manufactured in the same manner as Example 46 except that the epoxy resin composition prepared in Example 47 was used as a mold resin.

Example 48

An epoxy resin composition (thermosetting resin composition) of Example 48 was prepared in the same manner as Example 46 except that 2.56 parts by weight of the compound C12 was used instead of the compound C11, and packages (semiconductor devices) of Example 48 were manufactured in the same manner as Example 46 except that the epoxy resin composition prepared in Example 48 was used as a mold resin.

Example 49

An epoxy resin composition (thermosetting resin composition) of Example 49 was prepared in the same manner as Example 47 except that 2.56 parts by weight of the compound C12 was used instead of the compound C11, and packages (semiconductor devices) of Example 49 were manufactured in the same manner as Example 47 except that the epoxy resin composition prepared in Example 49 was used as a mold resin.

Example 50

An epoxy resin composition (thermosetting resin composition) of Example 50 was prepared in the same manner as Example 46 except that 3.36 parts by weight of the compound C13 was used instead of the compound C11, and packages (semiconductor devices) of Example 50 were manufactured in the same manner as Example 46 except that the epoxy resin composition prepared in Example 50 was used as a mold resin.

Example 51

An epoxy resin composition (thermosetting resin composition) of Example 51 was prepared in the same manner as Example 47 except that 3.36 parts by weight of the compound C13 was used instead of the compound C11, and packages (semiconductor devices) of Example 51 were manufactured in the same manner as Example 47 except that the epoxy resin composition prepared in Example 51 was used as a mold resin.

Example 52

An epoxy resin composition (thermosetting resin composition) of Example 52 was prepared in the same manner as Example 50 except that the compound C14 was used instead of the compound C13, and packages (semiconductor devices) of Example 52 were manufactured in the same manner as Example 46 except that the epoxy resin composition prepared in Example 52 was used as a mold resin.

Example 53

An epoxy resin composition (thermosetting resin composition) of Example 53 was prepared in the same manner as Example 51 except that the compound C14 was used instead of the compound C13, and packages (semiconductor devices) of Example 53 were manufactured in the same manner as Example 47 except that the epoxy resin composition prepared in Example 53 was used as a mold resin.

Example 54

An epoxy resin composition (thermosetting resin composition) of Example 54 was prepared in the same manner as Example 46 except that 2.85 parts by weight of the compound C15 was used instead of the compound C11, and packages (semiconductor devices) of Example 54 were manufactured in the same manner as Example 46 except that the epoxy resin composition prepared in Example 54 was used as a mold resin.

Example 55

An epoxy resin composition (thermosetting resin composition) of Example 55 was prepared in the same manner as Example 47 except that 2.85 parts by weight of the compound C15 was used instead of the compound C11, and packages (semiconductor devices) of Example 55 were manufactured in the same manner as Example 47 except that the epoxy resin composition prepared in Example 55 was used as a mold resin.

Example 56

An epoxy resin composition (thermosetting resin composition) of Example 56 was prepared in the same manner as Example 46 except that 3.32 parts by weight of the compound C16 was used instead of the compound C11, and packages (semiconductor devices) of Example 56 were manufactured in the same manner as Example 46 except that the epoxy resin composition prepared in Example 56 was used as a mold resin.

Example 57

An epoxy resin composition (thermosetting resin composition) of Example 57 was prepared in the same manner as Example 47 except that 3.32 parts by weight of the compound C16 was used instead of the compound C11, and packages (semiconductor devices) of Example 57 were manufactured in the same manner as Example 47 except that the epoxy resin composition prepared in Example 57 was used as a mold resin.

Example 58

An epoxy resin composition (thermosetting resin composition) of Example 58 was prepared in the same manner as Example 46 except that 3.01 parts by weight of the compound C17 was used instead of the compound C11, and packages (semiconductor devices) of Example 58 were manufactured in the same manner as Example 46 except that the epoxy resin composition prepared in Example 58 was used as a mold resin.

Example 59

An epoxy resin composition (thermosetting resin composition) of Example 59 was prepared in the same manner as Example 47 except that 3.01 parts by weight of the compound C17 was used instead of the compound C11, and packages (semiconductor devices) of Example 59 were manufactured in the same manner as Example 47 except that the epoxy resin composition prepared in Example 59 was used as a mold resin.

Comparative Example 10

An epoxy resin composition (thermosetting resin composition) of Comparative Example 10 was prepared in the same manner as Example 46 except that 3.69 parts by weight of the compound C18 was used instead of the compound C11, and packages (semiconductor devices) of Comparative Example 10 were manufactured in the same manner as Example 46 except that the epoxy resin composition prepared in Comparative Example 10 was used as a mold resin.

Comparative Example 11

An epoxy resin composition (thermosetting resin composition) of Comparative Example 11 was prepared in the same manner as Example 47 except that 3.69 parts by weight of the compound C18 was used instead of the compound C11, and packages (semiconductor devices) of Comparative Example 11 were manufactured in the same manner as Example 47 except that the epoxy resin composition prepared in Comparative Example 11 was used as a mold resin.

Comparative Example 12

An epoxy resin composition (thermosetting resin composition) of Comparative Example 12 was prepared in the same manner as Example 46 except that 4.34 parts by weight of the compound C19 was used instead of the compound C11, and packages (semiconductor devices) of Comparative Example 12 were manufactured in the same manner as Example 46 except that the epoxy resin composition prepared in Comparative Example 12 was used as a mold resin.

Comparative Example 13

An epoxy resin composition (thermosetting resin composition) of Comparative Example 13 was prepared in the same manner as Example 47 except that 4.34 parts by weight of the compound C19 was used instead of the compound C11, and packages (semiconductor devices) of Comparative Example 13 were manufactured in the same manner as Example 47 except that the epoxy resin composition prepared in Comparative Example 13 was used as a mold resin.

Comparative Example 14

An epoxy resin composition (thermosetting resin composition) of Comparative Example 14 was prepared in the same manner as Example 46 except that 3.10 parts by weight of the compound C20 was used instead of the compound C11, and packages (semiconductor devices) of Comparative Example 14 were manufactured in the same manner as Example 46 except that the epoxy resin composition prepared in Comparative Example 14 was used as a mold resin.

Comparative Example 15

An epoxy resin composition (thermosetting resin composition) of Comparative Example 15 was prepared in the same manner as Example 47 except that 3.10 parts by weight of the compound C20 was used instead of the compound C11, and packages (semiconductor devices) of Comparative Example 15 were manufactured in the same manner as Example 47 except that the epoxy resin composition prepared in Comparative Example 15 was used as a mold resin.

2-3 Characteristic Evaluation

For each of the epoxy resin compositions obtained in Examples 46 to 59 and Comparative Examples 10 to 15, characteristic evaluations (I) to (IV) were made as follows. Further, for each of the semiconductor packages obtained in Examples 46 to 59 and Comparative Examples 10 to 15, characteristic evaluations (V) and (VI) were made as follows.

(I) Spiral Flow

The spiral flow of each of the epoxy resin compositions was measured using a mold for spiral flow test according to EMMI-I-66, under the conditions of a mold temperature of 175° C., an injection pressure of 6.8 MPa, and a curing time of 2 minutes.

The spiral flow is a parameter of fluidity. Here, larger spiral flow means better fluidity.

(II) Curing Torque

The torque after 45 seconds at 175° C. of each of the epoxy resin compositions was measured using a curelastometer ("JSR curelastometer IV PS model" manufactured by Orientech Co., Ltd.). Here, larger curing torque means better curability.

(III) Residual Flow Percentage

Each of the epoxy resin compositions was preserved at 30° C. for 1 week in atmospheric air, and thereafter the spiral flow thereof was measured in the same manner described above. Then, the percentage (%) of the thus obtained spiral flow was determined on the basis of the initial spiral flow of the epoxy resin composition just after the preparation. Here, larger residual flow percentage means better storage stability.

(IV) Modulus of Elasticity 52 parts by weight of biphenyl type epoxy resin represented by the formula (23) as the compound (A), and 48 parts by weight of phenol aralkyl resin represented by the formula (24) as the compound (B) were blended with each of the compounds C11 to C20 as the curing accelerator (C) in an amount shown in Table 3, respectively, and then they were mixed at room temperature. The thus obtained each mixture was kneaded using a hot roll at 95° C. for 8 minutes, and was cooled and then ground, to thereby obtain an epoxy resin composition (thermosetting resin composition).

Next, the obtained each epoxy resin composition was molded by subjecting it to transfer molding under the conditions of a mold temperature of 175° C., an injection pressure of 7.4 MPa, and a curing time of 2 minutes, and then the molded product was after-cured at 175° C. for 8 hours, to thereby obtain a cured product.

The storage modulus of the cured product at 175° C. was measured using Rheovibron model DDV-25FP (manufactured by ORIENTEC CO.).

(V) Solder Cracking Resistance

Each of the 100-pin TQFP packages was left at 85° C. and at 85% relative humidity for 168 hours, and was then immersed in a solder bath at 260° C. for 10 seconds.

Thereafter, each package was observed under a microscope to determine whether or not cracking occurred in its surface. The occurrence rate of the cracking was obtained as a percentage (%) by calculating using the following formula.

Occurrence rate of cracking=(the number of packages in which cracking occurred/the total number of manufactured packages)×100

Here, smaller occurrence rate of cracking means better solder cracking resistance.

Further, an area where delamination occurred between the silicon chip and a cured product of the epoxy resin composition was measured using a reflectoscope. Then, the delamination ratio of the semiconductor package was obtained as a percentage by calculating using the following formula. Practically, an average value of 8 semiconductor packages was used for evaluation.

Delamination ratio=(area where delamination occurred)/(area of silicon chip)×100

Here, smaller delamination ratio means better solder cracking resistance.

(VI) Moisture Resistance Reliability

A voltage of 20 V was applied to each of the 16-pin DIP packages in water vapor at 125° C. and at 100% relative humidity, and each package was then checked whether or not conduction failure occurred therein. The time until the conduction failure occurred in 8 or more packages of the 15 packages was measured and the time was defined as a failure time.

In this regard, it is to be noted that the measuring time was 500 hours at longest, and in a case where the number of failed packages at that time was less than 8, the failure time was shown as "more than 500 hours (>500)". Here, longer failure time means better moisture resistance reliability. The results of the characteristic evaluations (I) to (VI) are shown in Table 3.

TABLE 3

| | Curing Accelerator | Blending Ratio of Curing Accelerator (parts by weight) | Epoxy Resin composition | | | | Package | | |
|---|---|---|---|---|---|---|---|---|---|
| | | | Spiral Flow (cm) | Curing Torque (N·m) | Residual Flow Percentage (%) | Modulus of Elasticity (M·Pa) | Solder Cracking Resistance (Occurrence Rate of Cracking: %) | Solder Cracking Resistance (Delamination Ratio: %) | Moisture Resistance Reliability (Failure Time: hr) |
| Example 46 | Compound C11 | 3.02 | 110 | 7.20 | 90 | 1.75+E01 | 0 | 0 | >500 |
| Example 47 | C11 | | 104 | 7.78 | 93 | | 0 | 0 | >500 |
| Example 48 | Compound C12 | 2.56 | 108 | 7.43 | 91 | 2.04+E01 | 0 | 0 | >500 |
| Example 49 | C12 | | 106 | 7.95 | 93 | | 0 | 0 | >500 |
| Example 50 | Compound C13 | 3.36 | 121 | 7.02 | 90 | 1.86+E01 | 0 | 0 | >500 |
| Example 51 | C13 | | 117 | 7.21 | 92 | | 0 | 0 | >500 |
| Example 52 | Compound C14 | 3.36 | 107 | 8.02 | 92 | 2.65+E01 | 5 | 0 | >500 |
| Example 53 | C14 | | 102 | 8.55 | 94 | | 5 | 0 | >500 |
| Example 54 | Compound C15 | 2.85 | 110 | 8.24 | 89 | 1.87+E01 | 0 | 0 | >500 |
| Example 55 | C15 | | 107 | 8.79 | 90 | | 0 | 0 | >500 |
| Example 56 | Compound C16 | 3.32 | 107 | 7.52 | 88 | 2.17+E01 | 0 | 0 | >500 |
| Example 57 | C16 | | 103 | 8.11 | 90 | | 0 | 0 | >500 |
| Example 58 | Compound C17 | 3.01 | 99 | 7.35 | 83 | 2.10+E01 | 0 | 0 | >500 |
| Example 59 | C17 | | 93 | 7.82 | 88 | | 0 | 0 | >500 |
| Com. Example 10 | Compound C18 | 3.69 | 86 | 9.10 | 60 | 3.24+E01 | 20 | 15 | >500 |
| Com. Example 11 | C18 | | 80 | 9.02 | 55 | | 20 | 15 | >500 |
| Com. Example 12 | Compound C19 | 4.34 | 75 | 6.55 | 65 | 2.75+E01 | 20 | 5 | 480 |
| Com. Example 13 | C19 | | 70 | 6.33 | 64 | | 20 | 5 | 480 |
| Com. Example 14 | Compound C20 | 3.10 | 96 | 6.65 | 45 | 2.76+E01 | 20 | 5 | 480 |
| Com. Example 15 | C20 | | 95 | 6.86 | 40 | | 20 | 5 | 480 |

As shown in Table 3, each of the epoxy resin compositions obtained in Examples 46 to 59 (epoxy resin compositions of the present invention) had extremely excellent curability, storage stability and fluidity. Further, since the modulus of elasticity of each of the cured products of the epoxy resin compositions of Examples 46 to 59 was low, each of the packages of the Examples 46 to 59 (semiconductor devices of the present invention) encapsulated with the respective cured product had excellent solder cracking resistance and moisture resistance reliability.

Further, the semiconductor devices manufactured in Examples 48 to 51, in which the compound C12 or the compound C13 was used as a curing accelerator had improved solder cracking resistance as compared with the semiconductor devices manufactured in Examples 52 and 53, in which the compound C14 was used as a curing accelerator. From this result, it is confirmed that by using a salt of trisubstituted phosphoniophenolate in which the hydroxyl group in the cation component is located in ortho position or meta position to the phosphorus atom, as a curing accelerator, an obtained semiconductor package can have improved solder cracking resistance as compared with the case where a salt of trisubstituted phosphoniophenolate in which the hydroxyl group in the cation component is located in para position to the phosphorus atom is used as a curing accelerator.

On the other hand, each of the epoxy resin compositions obtained in Comparative Examples 10 and 11 had poor storage stability. Further, since the modulus of elasticity of each of the cured products of the epoxy resin compositions of Comparative Examples 10 and 11 was high, each of the packages obtained in the Comparative Examples 10 and 11 had extremely poor solder cracking resistance.

Further, each of the epoxy resin compositions obtained in Comparative Examples 12 to 15 had extremely poor curability, storage stability and fluidity. Further, since the modulus of elasticity of each of the cured products of the epoxy resin compositions of the Comparative Examples 12 to 15 was high, each of the packages of the Comparative Examples 12 to 15 had poor solder cracking resistance.

Examples 60 to 66 and Comparative Examples 16 to 18

Epoxy resin compositions (thermosetting resin compositions) of Examples 60 to 66 and Comparative Examples 16 to 18 were prepared in the same manner as Examples 46, 48, 50, 52, 54, 56 and 58 and comparative Examples 10, 12 and 14, respectively, except that a mixture of 26 parts by weight of biphenyl type epoxy resin represented by the formula (23) and 28.5 parts by weight of biphenyl aralkyl type epoxy resin represented by the formula (25) as the compound (A), and 45.5 parts by weight of phenol aralkyl resin represented by the formula (24) as the compound (B) were used, and packages (semiconductor devices) of Examples 60 to 66 and Comparative Example 16 to 18 were manufactured in the same manner as Example 46 except that the epoxy resin compositions prepared in Examples 60 to 66 and comparative Examples 16 to 18 were used as a mold resin, respectively.

For each of the epoxy resin compositions and packages obtained in Examples 60 to 66 and Comparative Examples 16 to 18, characteristic evaluations were made. Their measurement results were substantially the same as those of Examples 46, 48, 50, 52, 54, 56 and 58 and Comparative Examples 10, 12 and 14 shown in Table 3, respectively.

Examples 67 to 73 and Comparative Examples 19 to 21

Epoxy resin compositions (thermosetting resin compositions) of Examples 67 to 73 and Comparative Examples 19 to 21 were prepared in the same manner as Examples 46, 48, 50, 52, 54, 56 and 58, and comparative Examples 10, 12 and 14, respectively, except that 54.5 parts by weight of biphenyl type epoxy resin represented by the formula (23) as the compound (A), and a mixture of 24 parts by weight of phenol aralkyl resin represented by the formula (24) and 21.5 parts by weight of biphenyl aralkyl type phenolic resin represented by the formula (26) as the compound (B) were used, and packages (semiconductor devices) of Examples 67 to 73 and Comparative Example 19 to 21 were manufactured in the same manner as Example 46 except that the epoxy resin compositions prepared in Examples 67 to 73 and Comparative Examples 19 to 21 were used as a mold resin, respectively.

For each of the epoxy resin compositions and packages obtained in Examples 67 to 73 and Comparative Examples 19 to 21, characteristic evaluations were made. Their measurement results were substantially the same as those of Examples 46, 48, 50, 52, 54, 56 and 58 and Comparative Examples 10, 12 and 14 shown in Table 3, respectively.

Examples 74 to 80 and Comparative Example 22

Resin compositions (thermosetting resin compositions) of Examples 74 to 80 and Comparative Example 22 were prepared by blending 100 parts by weight of bismaleimide resin composed of diaminodiphenylmethane (BMI-H made by K-I CHEMICAL, INDUSTRY Co., LTD.) with each of the compounds C11 to C17 and C20 as a curing accelerator at the blending ratio shown in Table 4, respectively, and homogeneously mixing them.

For each of the resin compositions obtained in Examples 74 to 80 and Comparative Example 22, gel time at 175° C. was measured. The measurement results and the blending ratio of each of the curing accelerators are shown in Table 4.

TABLE 4

| | Curing Accelerator | | |
|---|---|---|---|
| | Kind | Blending Ratio (parts by weight) | Gel Time (second) |
| Example 74 | Compound C11 | 3.02 | 30 |
| Example 75 | Compound C12 | 3.37 | 35 |
| Example 76 | Compound C13 | 3.65 | 38 |
| Example 77 | Compound C14 | 3.65 | 35 |
| Example 78 | Compound C15 | 3.65 | 38 |
| Example 79 | Compound C16 | 4.55 | 35 |
| Example 80 | Compound C17 | 4.30 | 32 |
| Com. Example 22 | Compound C20 | 3.10 | 40 |

As shown in Table 4, each of the resin compositions obtained in Examples 74 to 80 was immediately cured. On the other hand, the resin composition obtained in Comparative Example 22 was slowly and unsatisfactorily cured.

As has been described above, according to the curing accelerator of the present invention, it is possible to immediately cure curable resin compositions, and it is also possible to effectively prevent defects from occurring in cured products of the curable resin compositions even in a case where they are exposed to high temperature.

Further, the epoxy resin composition of the present invention has excellent curability, storage stability and fluidity.

Furthermore, even in a case where the semiconductor device of the present invention is exposed to high temperature, defects such as cracking, delamination and the like are hard to occur therein. Also, deterioration with age due to moisture absorption is hard to occur.

What is claimed is:

1. An epoxy resin composition comprising:
   a compound having two or more epoxy groups in one molecule,
   a compound having two or more phenolic hydroxyl groups in one molecule,
   and a curing accelerator for promoting the curing reaction of the epoxy resin composition,
   wherein the curing accelerator comprises trisubstituted phosphoniophenolate or a salt thereof, wherein the trisubstituted phosphoniophenolate is represented by the following general formula (1):

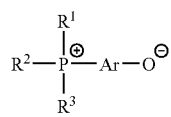
(1)

wherein $R^1$, $R^2$ and $R^3$ are the same as or different from one another, and each represents a substituted or unsubstituted monovalent aromatic group or a substituted or unsubstituted monovalent alkyl group; and Ar represents (i) an unsubstituted divalent aromatic group or (ii) a divalent aromatic group substituted with a single substituent, said substituent not being a hydroxyl group; further wherein in the case when said divalent aromatic group is a phenylene group, the oxyanion-$O^-$ is located in an ortho or meta position relative to the phosphorus atom.

2. An epoxy resin composition comprising:
   a compound having two or more epoxy groups in one molecule,
   a compound having two or more phenolic hydroxyl groups in one molecule, and a curing accelerator for promoting the curing reaction of the epoxy composition,
   wherein the curing accelerator comprises trisubstituted phosphoniophenolate or a salt thereof, wherein the trisubstituted phosphoniophenolate is represented by the following general formula (2):

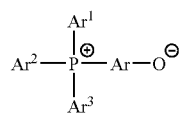
(2)

wherein $Ar^1$, $Ar^2$ and $Ar^3$ are the same as or different from one another, and each represents a substituted or unsubstituted monovalent aromatic group; and Ar represents (i) an unsubstituted divalent aromatic group or (ii) a divalent aromatic group substituted with a single substituent, said substituent not being a hydroxyl group; further wherein in the case when said divalent aromatic group is a phenylene group, the oxyanion-$O^-$ is located in an ortho or meta position relative to the phosphorus atom.

3. An epoxy resin composition comprising:
   a compound having two or more epoxy groups in one molecule,
   a compound having two or more phenolic hydroxyl groups in one molecule, and
   a curing accelerator for promoting the curing reaction of the epoxy resin composition, wherein the curing accelerator comprises trisubstituted phosphoniophenolate or a salt thereof, wherein the trisubstituted phosphoniophenolate is represented by the following general formula (3):

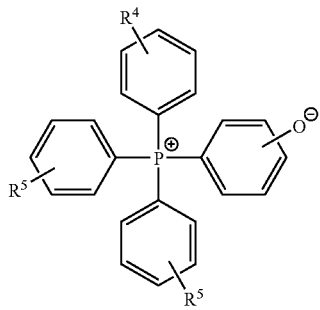

(3)

wherein $R^4$, $R^5$ and $R^6$ are the same as or different from one another, and each is selected from the group consisting of a hydrogen atom, a methyl group, a methoxy group and a hydroxyl group, further wherein the oxyanion-$O^-$ is located in an ortho or meta position relative to the phosphorus atom.

4. The epoxy resin composition as claimed in claim 1, wherein the salt of trisubstituted phosphoniophenolate is represented by the following general formula (4):

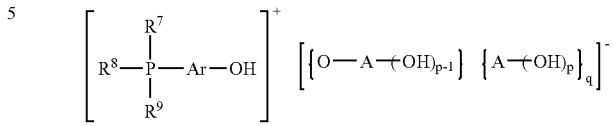

(4)

wherein $R^7$, $R^8$ and $R^9$ are the same as or different from one another, and each represents a substituted or unsubstituted monovalent aromatic group or a substituted or unsubstituted monovalent alkyl group; A represents a p-valent organic group containing group containing at least one aromatic ring and/or at least one heterocycle; and p is an integer of 2 to 8 and q is 0 to 2.

5. The epoxy resin composition as claimed in claim 1, wherein the salt of trisubstituted phosphoniophenolate is represented by the following general formula (5)

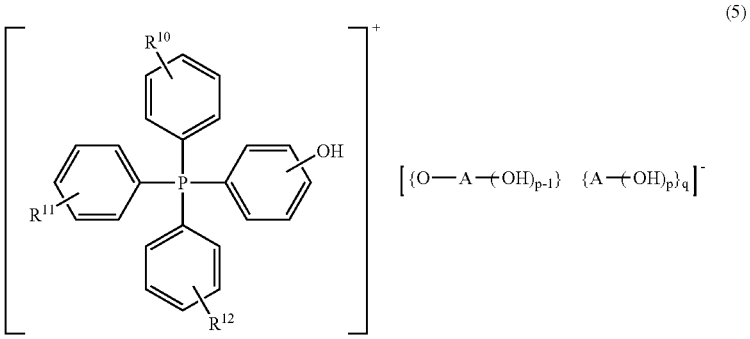

wherein $R^{10}$, $R^{11}$ and $R^{12}$ are the same as or different from one another, and each is selected from the group consisting of a hydrogen atom, a methyl group, a methoxy group and a hydroxyl group; A represents a p-valent organic group containing at least one aromatic ring and/or at least one heterocycle; and p is an integer of 2 to 8 and q is 0 to 2.

6. The epoxy resin composition as claimed in claim 1, wherein the salt of trisubstituted phosphoniophenolate is represented by the following general formula (6) or (7):

(6)

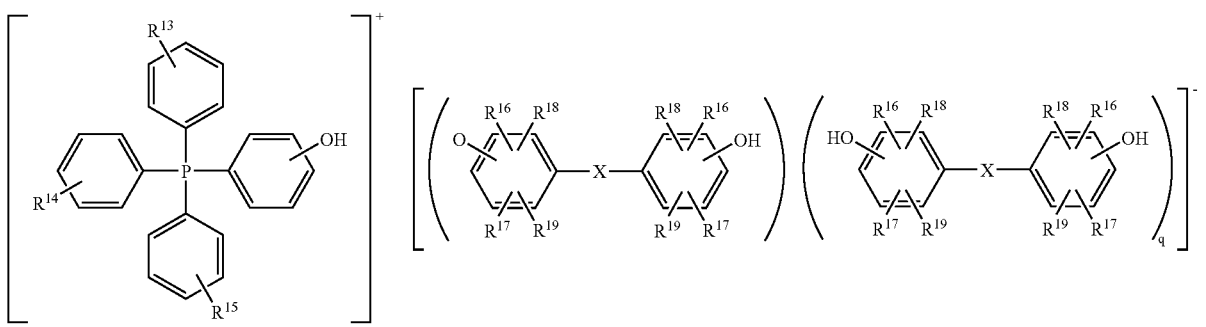

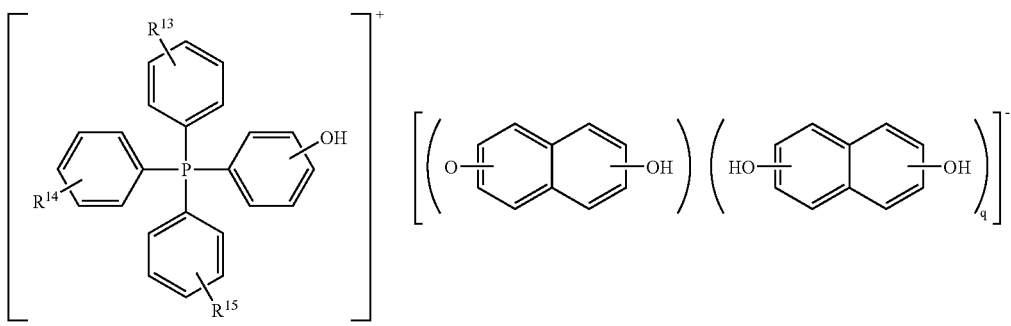
(7)

wherein $R^{13}$, $R^{14}$ and $R^{15}$ are the same as or different from one another, and each is selected from the group consisting of a hydrogen atom, a methyl group, a methoxy group and a hydroxyl group; $R^{16}$, $R^{17}$, $R^{18}$ and $R^{19}$ are the same as or different from one another, and each is selected from the group consisting of a hydrogen atom, a halogen atom and a monovalent organic group having 1 to 6 carbon atoms; X represents a single bond, an ether group, a sulfone group, a sulfide group, a carbonyl group or a divalent organic group having 1 to 13 carbon atoms; and q is 0 to 2.

7. The epoxy resin composition as claimed in claim 1, wherein the compound having two or more epoxy groups in one molecule contains as a main ingredient at least one of epoxy resins represented by the following general formulas (8) and (9):

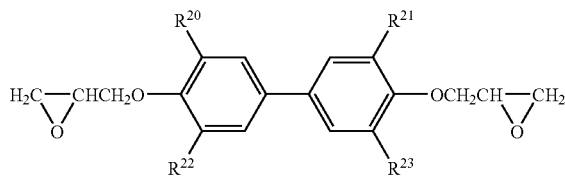
(8)

wherein $R^{20}$, $R^{21}$, $R^{22}$ and $R^{23}$ are the same as or different from one another, and each is selected from the group consisting of a hydrogen atom, a linear or cyclic alkyl group having 1 to 6 carbon atoms, a phenyl group and a halogen atom; and

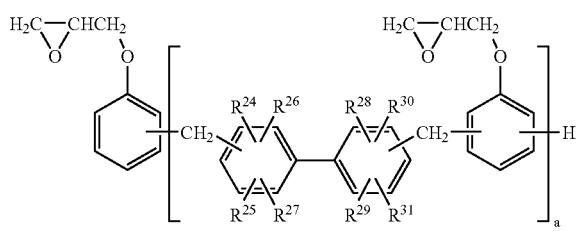
(9)

wherein $R^{24}$ to $R^{31}$ are the same as or different from one another, and each is selected from the group consisting of a hydrogen atom, an alkyl group having 1 to 4 carbon atoms and a halogen atom; and a is an integer of 1 or more.

8. The epoxy resin composition as claimed in claim 7, wherein a is an integer of 1 to 10.

9. The epoxy resin composition as claimed in claim 1, wherein the compound having two or more phenolic hydroxyl groups in one molecule contains as a main ingredient at least one of phenolic resins represented by the following general formulas (10) and (11):

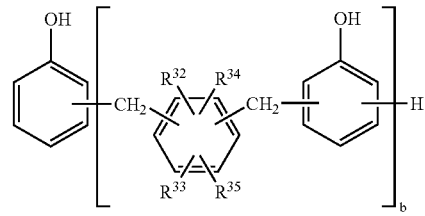
(10)

wherein $R^{32}$ to $R^{35}$ are the same as or different from one another, and each is selected from the group consisting of a hydrogen atom, an alkyl group having 1 to 4 carbon atoms and a halogen atom; and b is an integer of 1 or more; and

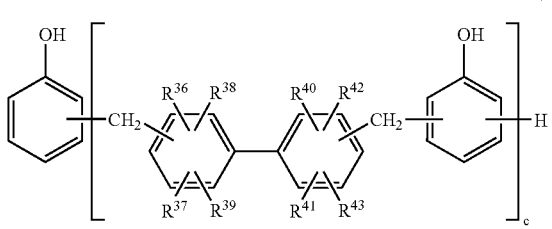
(11)

wherein $R^{36}$ to $R^{43}$ are the same as or different from one another, and each is selected from the group consisting of a hydrogen atom, an alkyl group having 1 to 4 carbon atoms and a halogen atom; and c is an integer of 1 or more.

10. The epoxy resin composition as claimed in claim 9, wherein b is an integer of 1 to 10.

11. The epoxy resin composition as claimed in claim 9, wherein c is an integer of 1 to 10.

12. The epoxy resin composition as claimed in claim 1, wherein the content of the curing accelerator is in the range of 0.01 to 10 wt %.

13. The epoxy resin composition as claimed in claim 1, further comprising an inorganic filler.

14. The epoxy resin composition as claimed in claim 13, wherein the inorganic filler is fused silica.

15. The epoxy resin composition as claimed in claim 13, wherein the inorganic filler is in the form of granules or particles.

16. The epoxy resin composition as claimed in claim 15, wherein the average particle size of the inorganic filler is in the range of 1 to 100 μm.

17. The epoxy resin composition as claimed in claim 13, wherein the content of the inorganic filler is in the range of 200 to 2,400 parts by weight per 100 parts by weight of the total amount of the compound having two or more epoxy groups in one molecule and the compound having two or more phenolic hydroxyl groups in one molecule.

18. A semiconductor device manufactured by encapsulating at least one semiconductor element with a cured product of the epoxy resin composition claimed in claim 13.

* * * * *